United States Patent
Tran et al.

(10) Patent No.: US 8,626,530 B1
(45) Date of Patent: Jan. 7, 2014

(54) SYSTEM AND METHOD FOR EXPRESS REFILL

(75) Inventors: Quynh Chieu H. Tran, Chicago, IL (US); Satya Chandra Mouli Kota, Prospect Heights, IL (US); Tim McCauley, Libertyville, IL (US)

(73) Assignee: Walgreen Co., Deerfield, IL (US)

( * ) Notice: Subject to any disclaimer, the term of this patent is extended or adjusted under 35 U.S.C. 154(b) by 0 days.

(21) Appl. No.: 13/367,507

(22) Filed: Feb. 7, 2012

Related U.S. Application Data

(63) Continuation of application No. 12/869,983, filed on Aug. 27, 2010.

(51) Int. Cl.
G06Q 50/00 (2012.01)
G06Q 50/22 (2012.01)
G06Q 50/24 (2012.01)

(52) U.S. Cl.
CPC .............. G06Q 50/22 (2013.01); G06Q 50/24 (2013.01)
USPC .................................................. 705/2; 705/3

(58) Field of Classification Search
CPC ............................ G06Q 50/22; G06Q 50/24
USPC ........................................................ 705/2, 3
See application file for complete search history.

(56) References Cited

U.S. PATENT DOCUMENTS

| | | | |
|---|---|---|---|
| 6,202,923 B1 | 3/2001 | Boyer et al. | |
| 6,871,783 B2 | 3/2005 | Kaafarani et al. | |
| 7,058,584 B2 | 6/2006 | Kosinski et al. | |
| 7,630,908 B1 * | 12/2009 | Amrien et al. | 705/3 |
| 7,769,601 B1 | 8/2010 | Bleser et al. | |
| 8,027,847 B1 | 9/2011 | Francis et al. | |
| 8,055,515 B2 * | 11/2011 | Kusakabe | 705/3 |
| 2002/0032582 A1 | 3/2002 | Feeney et al. | |
| 2004/0019794 A1 * | 1/2004 | Moradi et al. | 713/185 |
| 2004/0049476 A1 | 3/2004 | Sai et al. | |
| 2005/0060200 A1 * | 3/2005 | Kobylevsky et al. | 705/2 |
| 2009/0006141 A1 | 1/2009 | Karr | |
| 2009/0150176 A1 | 6/2009 | Gejdos et al. | |
| 2009/0210255 A1 * | 8/2009 | Leon | 705/3 |
| 2010/0324936 A1 * | 12/2010 | Vishnubhatla et al. | 705/3 |
| 2011/0125521 A1 * | 5/2011 | Dhoble | 705/2 |

OTHER PUBLICATIONS

Jwordsmith, Using the Red Laser Barcode Scanner to Add Batches of Books to LibraryThinsg.com, Feb. 25, 2010.*

Office action for U.S. Appl. No. 12/869,983 issued Apr. 26, 2012.

(Continued)

*Primary Examiner* — Neha Patel

(74) *Attorney, Agent, or Firm* — Cary M. Pumphrey; Randall G. Rueth; Marshall, Gerstein & Borun LLP

(57) ABSTRACT

A system and method may provide a refill interface and service which allow a customer to order refills of one or more prescription medications in a quick and hassle-free manner from a mobile device. The customer provides prescription data from a barcode image that includes a number associated with an order. The prescription number is received by a server and a pickup store and a pickup time are determined. The user is provided an opportunity to select a new pickup store and/or a new pickup time. The refill system and method provide the service through a series of web pages and/or via an application running on a mobile device.

19 Claims, 23 Drawing Sheets

(56) References Cited

OTHER PUBLICATIONS

Office Action for U.S. Appl. No. 12/869,983, issued Apr. 26, 2012.
Office Action for U.S. Appl. No. 13/367,507, issued May 11, 2012.
Office Action for U.S. Appl. No. 13/367,507, issued Oct. 18, 2012.
Office Action for U.S. Appl. No. 13/367,507, issued Mar. 15, 2013.
Jwordsmith (Using The Red Laser Barcode Scanner to Add Batches of Books to LibraryThing.com, dated Feb. 25, 2010.).

* cited by examiner

300

Walgreens → Store Locator | Log in to access your profile or register
Username  Password [GO] + need help?

🛒 pharmacy  ⓕ clinic  ♥ health info  📷 photo  🗂 shop    search [      ] [GO]
beauty | health & well being | home medical | personal care | contact lens | health shops | seasonal | view all [save] [weekly ad]
We now fill 90-day prescriptions. → Get the details                             shopping list  ♥ cart (0)

Order Prescriptions
> Refill Prescriptions
> New Prescriptions
> Transfer Prescriptions

Prescription Services
> Auto Refills
> Email Reminders
> Print Prescription Records
> Update Health History  304
> Prescription History

Drug Information
> Drug Information
> Check Drug Interactions

Answers and Ideas
> Ask a Pharmacist
> Health Newsletters
> Health Corner TV
> Recipes

Convenience Services
> Caregivers
> ExpressPay
> Immunizations
> Large Print Labels
> Medicare Facts and Report
> Medicare Compounding
> Medicare Flavoring
> Multilingual Services
> Specialty Pharmacy

Health Shops
> Allergy
> Blood Pressure
> Diabetes
> Flu
> View All

Home > Pharmacy
In-Store Express Refills

You can use Express Refills if the prescription number is from your last refill and was picked up in-store.

Enter Prescription Number(s)

Prescription #1 (e.g. 1234567-12345)
[1234567-12345]   See example
Prescription #2
[           ] 312
Prescription #3
[           ]                              + Add more prescriptions Enter your email address if you would like to be notified when your prescription is ready for pickup.
If we already have one on file for you, an email will be sent and you can skip this step.

Email Address
[           ] (optional)                           ( CONTINUE )
← Cancel We don't rent or sell your information.
Walgreens Online Privacy and Security Policy

FIG. 12A
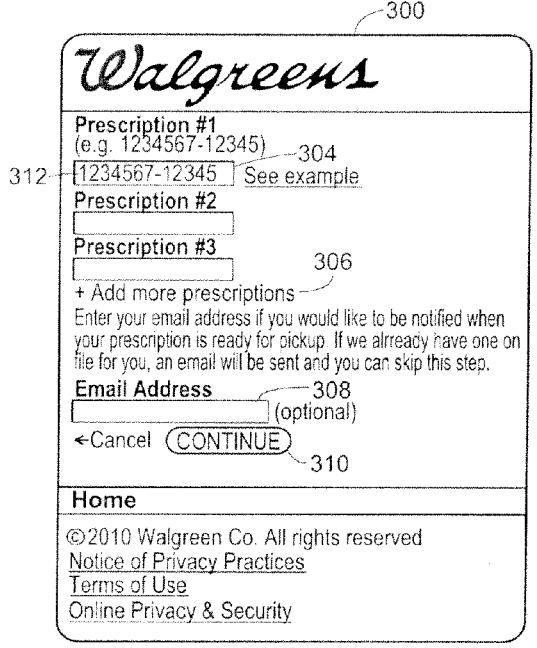
FIG. 12B
FIG. 12C

Walgreens

Pick up Details

We will make every effort to have your order ready by the following date and time:

Thursday, Aug.5, 2010 at 10:00 AM

Change pick up time

| Walgreens Pharmacy<br>Store 1234<br>Chicago, IL60606<br>123-123-4567 (Adams & Wells) | Pharmacy Hours<br>M-F: 8:00 AM - 6:00 PM<br>Sat: CLOSED<br>San: CLOSED |

334 → Walgreens Pharmacy / Store 1234
336 → 123-123-4567 (Adams & Wells)
330 (bracket)

Store Details  340
Change Store

If you provided an email address with your order or if we have one on file for the requested prescriptions, you will receive an email when your order is ready for pickup.

←Cancel (SUBMIT) —342

Home

©2010 Walgreen Co. All rights reserved
Notice of Privacy Practices
Terms of Use
Online Privacy & Security

Walgreens

Choose pick up date time

Select a date
[Mon, Aug 9, 2010 ▼] [Update]

Click the "Update" button above to calculate the correct pickup times for your selected date.

Select a time
[10:00 AM ▼]

←Cancel (CONTINUE)

Walgreens Pharmacy
200 W Adams
Chicago, IL60606
123-123-4567
(Adams & Wells)

Pharmacy Hours
M-F: 8:00 AM - 6:00 PM
Sat: CLOSED
San: CLOSED

Home

©2010 Walgreen Co. All rights reserved
Notice of Privacy Practices

Walgreens

We will make every effort to have your order ready by the following date and time:

Monday, Aug.9, 2010 at 10:00 AM
Walgreens Pharmacy
Store 1234
Chicago, IL60606
123-123-4567 (Adams & Wells)   Pharmacy Hours
M-F: 8:00 AM - 6:00 PM
Sat: CLOSED
San: CLOSED
Store Details 364 (bracket)

If you provided an email address with your order or if we have one on file for the requested prescriptions, you will receive an email when your order is ready for pickup.

Home

©2010 Walgreen Co. All rights reserved
Notice of Privacy Practices
Terms of Use
Online Privacy & Security
Powered by Usablenet
Help/Feedback

FIG. 12F

SYSTEM AND METHOD FOR EXPRESS REFILL

CROSS-REFERENCE TO RELATED APPLICATION

This application is a continuation of U.S. application Ser. No. 12/869,983, filed Aug. 27, 2010, the disclosure of which is hereby incorporated herein by reference in its entirety for all purposes.

TECHNICAL FIELD

The present disclosure generally relates to a system and method for refilling prescription medications using a camera in a web enabled device to scan a barcode and decode a prescription number.

BACKGROUND

While some medications prescribed to patients may be taken only for a brief period of time, other medications may be taken for extended periods of time. For convenience, when a doctor prescribes a medication that will be taken over an extended period, the doctor may write the prescription such that a pharmacy can refill the prescription one or more times without requiring renewed authorization from the doctor (i.e., without requiring a new prescription). When a patient runs out of the prescribed medication (or slightly before), the patient may contact the pharmacy at which the prescription was originally filled and request a refill, if there are any refills remaining.

In the past, a patient (or customer) wishing to order a refill of a prescription medication called the pharmacy or visited the pharmacy to ask for the refill in person. In some instances, a patient could request a refill of a prescription medication by mail or by facsimile. More recently, pharmacies have implemented internet-based interfaces (i.e., web sites) through which a patient could request a refill. To access the web pages through which prescription refills may be requested, a patient must be logged into a user profile. Generally, though not always, the user profile is associated with only one person, and the user can order refills only of the prescriptions associated with his profile. Some systems allow for a profile to be associated with multiple people (e.g., family members, patients in the charge of a caregiver, etc.), but this requires additional configuration steps, such as sending and responding to requests for permission, that often must be coordinated between multiple people.

In any event, the systems currently in place require a user who wishes to order a prescription refill to log into the system. This requires the patient to input a user name or email address and a password. For some patients, remembering the user name or password may be difficult and, if the patient does not have access to the information, the login requirement may prevent access to the system entirely. Even in cases where the patient knows (or has access to) the user name and password, entering the log-in information may be an impediment, especially for users attempting to order refills through a mobile device, many of which have input mechanisms that are difficult or, at least, inconvenient to use. Further, to order refills of prescriptions related to multiple patients, the systems often require a customer to have access to multiple profiles, require the customer to contact the pharmacy by alternate means, or to log into multiple profiles using an associated user name and password for each.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment of thereof. Further, wherever possible, the following description refers to the reference numerals included in the following figures, in which features depicted in multiple figures are designated with consistent reference numerals.

FIG. 6 depicts data entered into the express refill web page of FIG. 4;

FIG. 7 depicts an order review web page transmitted by the web server of FIG. 1D;

FIG. 8 depicts a store selection web page transmitted by the web server of FIG. 1D;

FIG. 12A depicts a second embodiment of the landing web page of FIG. 2;

FIG. 12B depicts a second embodiment of the pharmacy web page of FIG. 3;

FIG. 12C depicts a second embodiment of the express refill web page of FIG. 4;

FIG. 12D depicts a second embodiment of the order review web page of FIG. 7;

FIG. 12E depicts a pickup selection web page in accordance with an embodiment of the described embodiments;

FIG. 12F depicts a second embodiment of the order summary web page of FIG. 9;

DETAILED DESCRIPTION

Figure 1A:
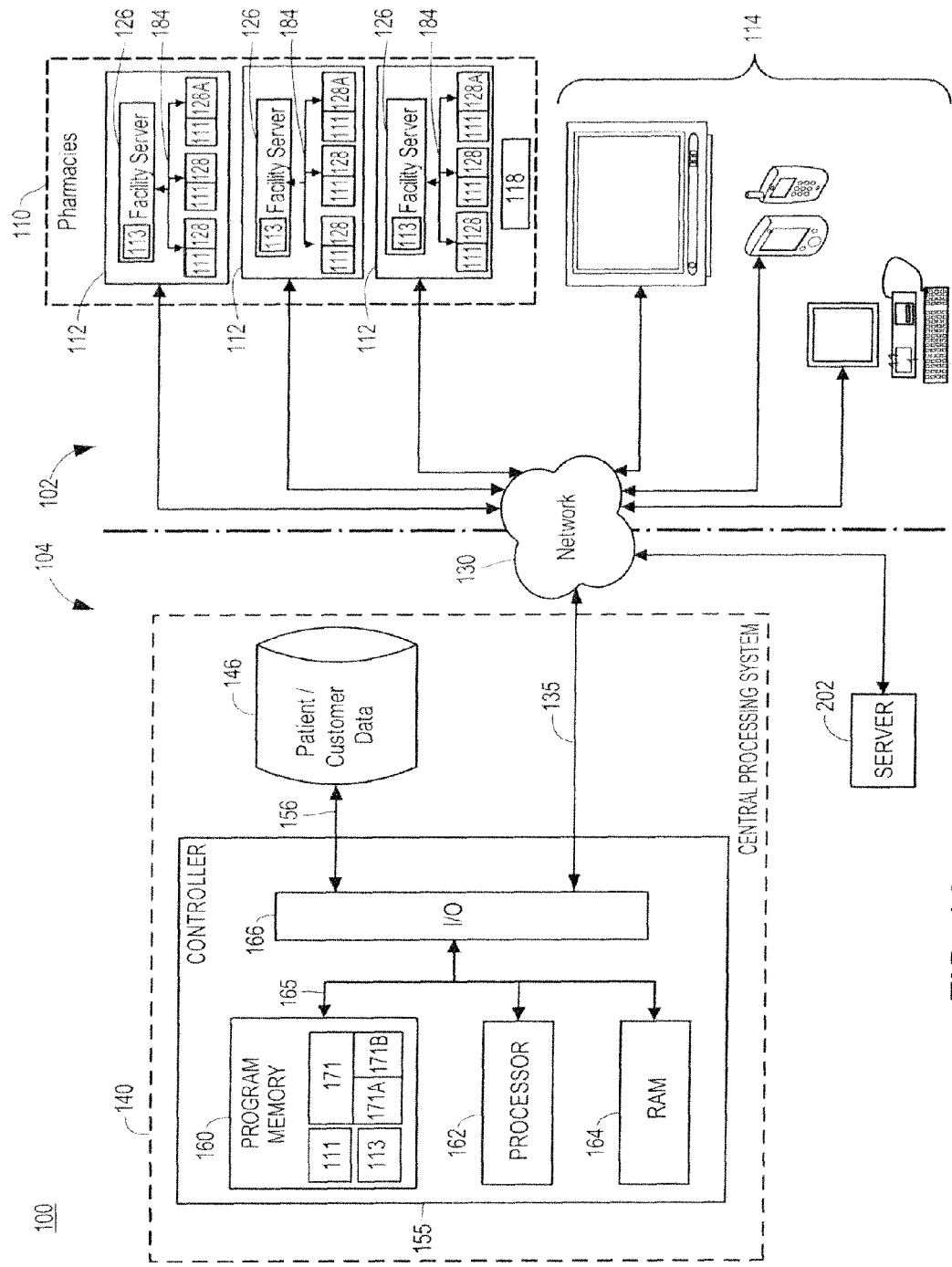
FIG. 1A illustrates a block diagram of a computer network and system on which an exemplary express refill system and method may operate in accordance with the described embodiments.
Figure 1B:
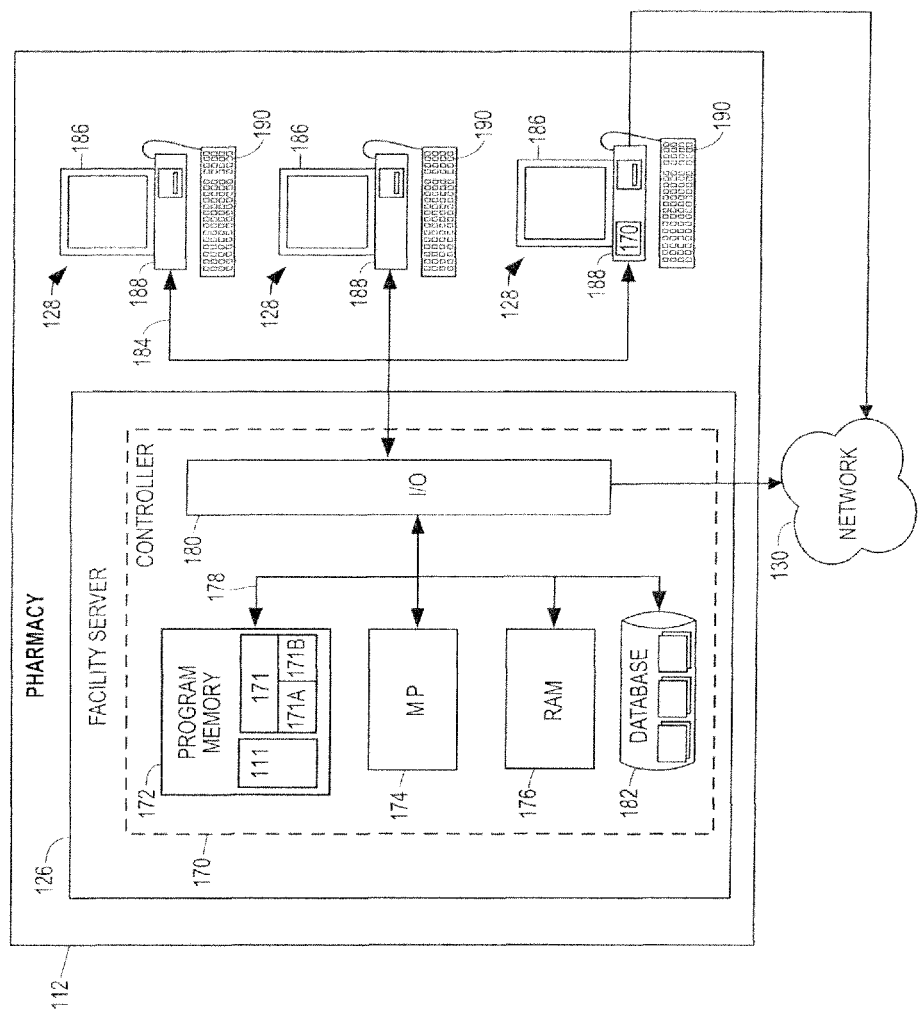
FIG. 1B illustrates a block diagram of a computer server and computer terminals on which an exemplary express refill system and method may operate.

FIGS. 1A and 1B illustrate various aspects of an exemplary architecture implementing an express refill system 100. In particular, FIG. 1A illustrates a block diagram of the exemplary express refill system 100. The high-level architecture includes both hardware and software applications, as well as various data communications channels for communicating data between the various hardware and software components. The express refill system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists, technicians, and other pharmacy personnel, referred to collectively herein simply as "pharmacists" (not shown), use the pharmacy workstations 128 to access customer information, enter new prescriptions, access insurance and payment information and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. Retail network 110 may also include one or more warehouses or central-filling facilities 118. The warehouses or central-filling facilities 118 may distribute medications to the various retail pharmacies 112 in the retail network 110, or may distribute medications directly to customers. Web-enabled devices 114 (e.g., personal computers, cellular phones, smart phones, web-enabled televisions, etc.) may be communicatively connected to pharmacies 112 and the system 140 through a digital network 130, as described below.

Returning now to FIG. 1A, those of ordinary skill in the art will recognize that the front-end components 102 could also comprise a plurality of facility servers 126 disposed at the plurality of pharmacies 112 instead of, or in addition to, a plurality of pharmacy workstations 128. Each of the pharmacies 112 may include one or more facility servers 126 that may facilitate communications between the web-enabled devices 114 and the back-end components 104 via a digital network 130, described below, and between the terminals 128, 128A of the pharmacies 112 via the digital network 129, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126, and vice versa. Moreover, environments other than the pharmacies 112, such as the kiosks, call centers, and Internet interface terminals may employ the workstations 128, the web-enabled devices 114, and the servers 126. As used herein, the term "pharmacy" refers to any of these points of contact (e.g., call centers, kiosks, Internet interface terminals, etc.) in addition to the retail pharmacies 112, etc. described above.

The front-end components 102 communicate with the back-end components 104 via the digital network 130. One or more of the front-end components 102 may be excluded from communication with the back-end components 104 by configuration or by limiting access due to security concerns. For example, the web enabled devices 114 may be excluded from direct access to the back-end components 104. In some embodiments, the pharmacies 112 may communicate with the back-end components via the digital network 130. In other embodiments, the pharmacies 112 and web-enabled devices 114 may communicate with the back-end components 104 via the same digital network 130, but digital access rights, IP masking, and other network configurations may deny access of the web-enabled devices 114.

The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. In addition to one or more web servers 202 (described below), the back-end components 104 include a central processing system 140 within a central processing facility, such as, for example, the central processing facility described in U.S. patent application Ser. No. 12/271,686 entitled "DISTRIBUTED PHARMACY PRESCRIPTION PROCESSING SYSTEM" the entire disclosure of which is incorporated by reference herein. Of course, the pharmacies 112 may be communicatively connected to different back-end components 104 having one or more functions or capabilities that are similar to the central processing system 140 (e.g., a processing system 141, 142). The central processing system 140 may include one or more computer processors 162 adapted and configured to execute various software applications and components of the express refill system 100, in addition to other software applications, such as a medication management system. The central processing system 140 further includes a database 146. The database 146 is adapted to store data related to the operation of the express refill system 100 (e.g., patient profile data including diagnoses, past healthcare product and medication purchases, prescription histories, etc.) The central processing system 140 may access data stored in the database 146 when executing various functions and tasks associated with the operation of the express refill system 100.

Although the express refill system 100 is shown to include a central processing system 140 in communication with three pharmacies 112, and various web-enabled devices 114 it should be understood that different numbers of processing systems, pharmacies, and devices may be utilized. For example, the digital network 130 (or other digital networks, not shown) may interconnect the system 100 to a plurality of included central processing systems 140, hundreds of pharmacies 112, and thousands of web-enabled devices 114. According to the disclosed example, this configuration may provide several advantages, such as, for example, enabling near real-time uploads and downloads of information as well as periodic uploads and downloads of information. This provides for a primary backup of all the information generated in the express refill process. Alternatively, some of the pharmacies 112 may store data locally on the facility server 126 and/or the workstations 128.

FIG. 1A also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner.

The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

FIG. 1B depicts one possible embodiment of the front-end components 102 located in one or more of the pharmacies 112 from FIG. 1A. Although the following description addresses the design of the pharmacies 112, it should be understood that the design of one or more of the pharmacies 112 may be different from the design of others of the pharmacies 112. Also, each of the pharmacies 112 may have various different structures and methods of operation. It should also be understood that while the embodiment shown in FIG. 1B illustrates some of the components and data connections that may be present in a pharmacy 112, it does not illustrate all of the data connections that may be present in a pharmacy 112. For exemplary purposes, one design of a pharmacy is described below, but it should be understood that numerous other designs may be utilized.

Each of the pharmacies 112 has one or more pharmacy workstations 128 and/or a facility server 126. The digital network 184 operatively connects the facility server 126 to the plurality of workstations 128 and/or to the web-enabled devices 114. The digital network 184 may be a wide area network (WAN), a local area network (LAN), or any other type of digital network readily known to those persons skilled in the art. The digital network 130 may operatively connect the facility server 126, the workstations 128, and/or the web-enabled devices 114 to the central processing system 140.

Each workstation 128, client device terminal 128A, or facility server 126 includes a controller 170. Similar to the controller 155 from FIG. 1A, the controller 170 includes a program memory 172, a microcontroller or a microprocessor (MP) 174, a random-access memory (RAM) 176, and an input/output (I/O) circuit 180, all of which are interconnected via an address/data bus 178. In some embodiments, the controller 170 may also include, or otherwise be communicatively connected to, a database 182. The database 182 (and/or the database 146 of FIG. 1A) includes data such as customer records, insurer information records, and other rules and miscellaneous information. As discussed with reference to the controller 155, it should be appreciated that although FIG. 1B depicts only one microprocessor 174, the controller 170 may include multiple microprocessors 174. Similarly, the memory of the controller 170 may include multiple RAMs 176 and multiple program memories 172. Although the FIG. depicts the I/O circuit 180 as a single block, the I/O circuit 180 may include a number of different types of I/O circuits. The controller 170 may implement the RAM(s) 176 and the program memories 172 as semiconductor memories, magnetically readable memories, and/or optically readable memories, for example.

Either or both of the program memories 160 (FIG. 1A) and 172 may also contain machine-readable instructions (i.e., software) 171, for execution within the processors 162 (FIG. 1A) and 174, respectively. The software 171 may perform the various tasks associated with operation of the pharmacy or pharmacies, and may be a single module 171 or a plurality of modules 171A, 171B. While the software 171 is depicted in FIGS. 1A and 1B as including two modules, 171A and 171B, the software 171 may include any number of modules accomplishing tasks related to pharmacy operation including, for example, receiving prescription orders, managing prescription workflow, etc.

In addition to the controller 170, the workstations 128 and the web-enabled devices 114 may further include a display 186 and a keyboard 190 as well as a variety of other input/output devices (not shown) such as a scanner, printer, mouse, touch screen, track pad, track ball, isopoint, voice recognition system, digital camera, bar code scanner, RFID reader, etc. A pharmacy employee may sign on and occupy each workstation 128 or client device terminal 128A to assist the pharmacy employee in performing his or her duties. Pharmacy employees may sign onto the workstation 128 or the client device terminal 128A using any available technique, such as entering a user name and password. If a pharmacy employee signs on to the system using a client device terminal 128A, the network 184 communicates this information to the facility server 126, so that the controller 170 may identify which pharmacy employees are signed onto the system 100 and which workstation 128 or client device terminal 128A the employee is signed onto. This may be useful for record keeping and/or monitoring the pharmacy employees' productivity as well as in record-keeping or routing prescription transfers to pharmacists who are authorized to accept controlled prescriptions, or other transfer tasks requiring various levels of authority or access corresponding to a login identification or other information.

Various software applications resident in the front-end components 102 and the back-end components 104 implement functions related to pharmacy operation, and provide various user interface means to allow users (i.e., pharmacists and/or customers) to access the system 100. One or more of the front-end components 102 and/or the back-end components 104 may include a user-interface application 111 for allowing a user, such as the patient, the pharmacist, or a customer service representative, to input and view data associated with the system 100, and to interact with the express refill system described below. In one embodiment, the user interface application 111 is a web browser client, and the facility server 126 or the central processing system 140 implements a server application 113 for providing data to the user interface application 111. However, the user interface application 111 may be any type of interface, including a proprietary interface, and may communicate with the facility server 126 or the central processing system 140 using any type of protocol including, but not limited to, file transfer protocol (FTP), telnet, hypertext-transfer protocol (HTTP), etc. Moreover, some embodiments may include the user interface application 111 running on one of the web-enabled devices 114 (as when a patient is accessing the system), while other embodiments may include the application 111 running on one of the workstations 128 in a pharmacy 112. The information sent to the workstations 128 and to the web-enabled devices 114 from the facility server 126 and/or the central processing system 140 includes data retrieved from the database 146 and/or the database 182. The central processing system 140 and/or the facility server 126 may implement any known protocol compatible with the user-interface application 111 running on the workstations 128 and the web-enabled devices 114 and adapted to the purpose of receiving and providing the necessary patient/customer information during the express refill process.

Figure 1C:
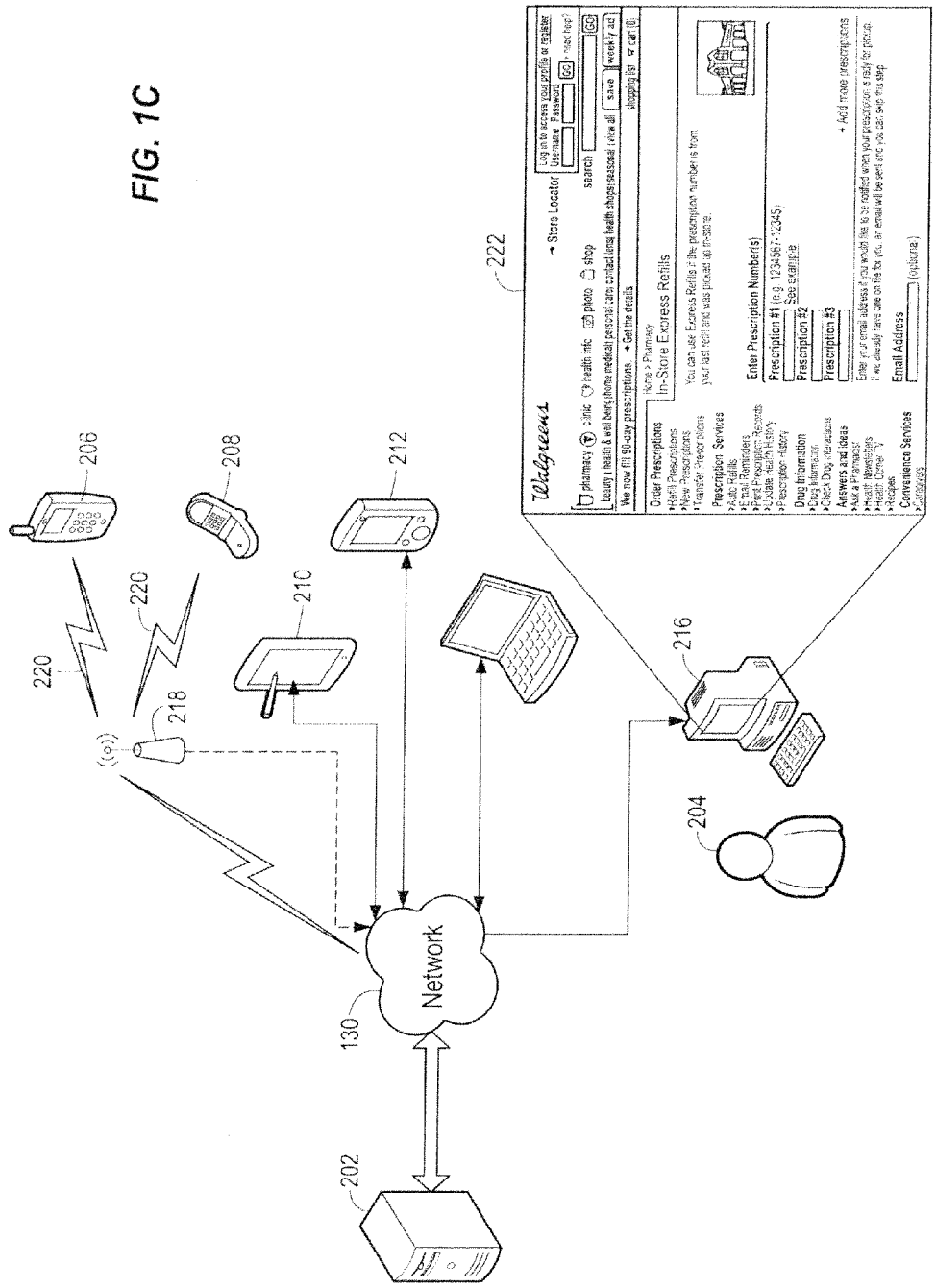
FIG. 1C illustrates web-enabled devices and associated equipment that may operate with a network and a server.
Figure 10:
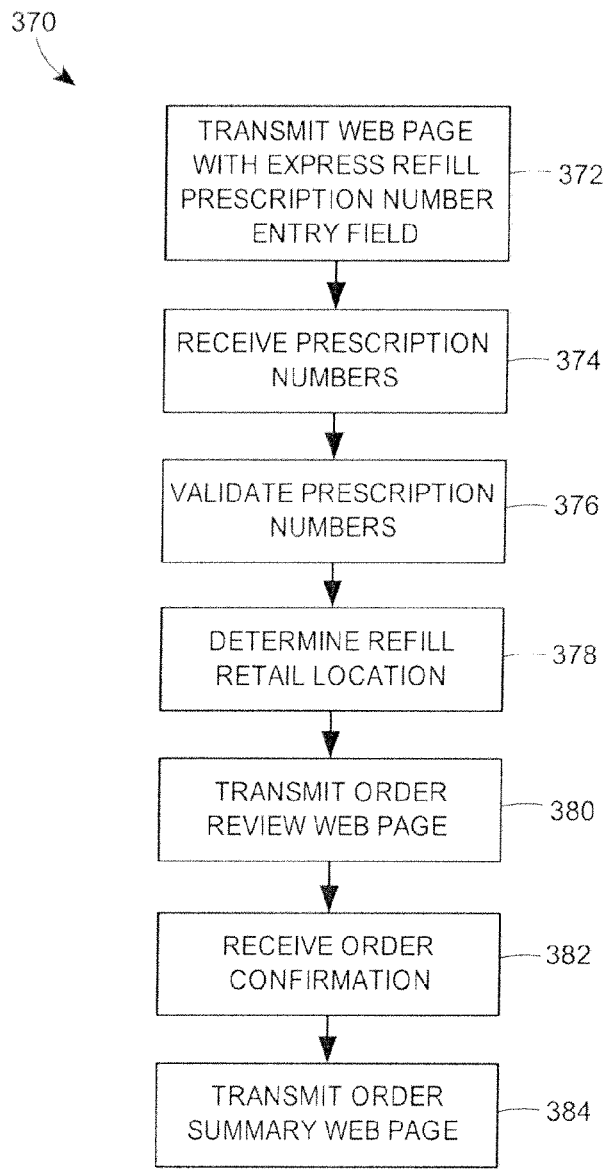
FIG. 10 illustrates an exemplary method implementing the express refill system in accordance with the presently described embodiments.

For purposes of implementing the express refill system 100, the customer interacts with pharmacy systems (e.g., the central processing system 140) via a plurality of web pages. FIG. 10 depicts a web server 202 connected via the network 130 to a plurality of web-enabled devices through which a user 204 may initiate and interact with the express refill system 100. The web enabled devices may include, by way of example, a smart-phone 206, a web-enabled cell phone 208, a tablet computer 210, a personal digital assistant (PDA) 212, a laptop computer 214, a desktop computer 216, a portable media player (not shown), etc. Of course, any web-enabled device appropriately configured may interact with the express refill system 100. The web-enabled devices 206-216 need not necessarily communicate with the network 130 via a wired connection. In some instances, the web enabled devices 206-216 may communicate with the network 130 via wireless signals 220 and, in some instances, may communicate with the network 130 via an intervening wireless or wired device 118, which may be a wireless router, a wireless repeater, a base transceiver station of a mobile telephony provider, etc. Each of the web-enabled devices 206-216 may interact with the web server 202 to receive web pages, such as the web page 222 depicted in FIG. 1C, for display on a display associated with the web-enabled device 206-216. It will be appreciated that although only one web server 202 is depicted in FIG. 10, multiple web servers 202 may be provided for the purpose of distributing server load, serving different web pages, implementing different portions of the pharmacy web interface, etc.

Figure 1D:
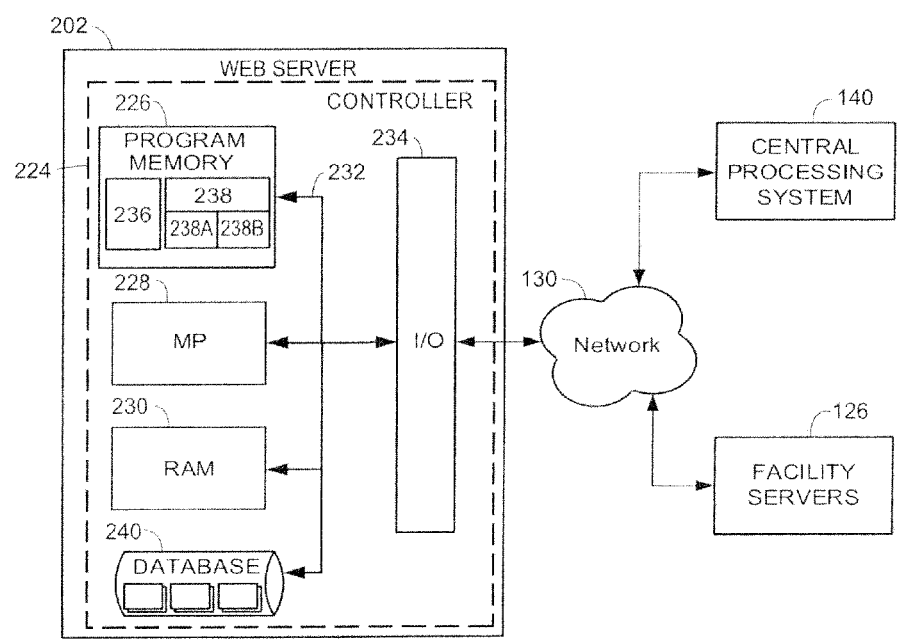
FIG. 1D illustrates a block diagram of an exemplary web server.

Turning now to FIG. 1D, the web server 202, like the facility server 126, includes a controller 234. Similar to the controllers 155 and 170, the controller 234 includes a program memory 226, a microcontroller or a microprocessor (MP) 228, a random-access memory (RAM) 230, and an input/output (I/O) circuit 234, all of which are interconnected via an address/data bus 232. In some embodiments, the controller 234 may also include, or otherwise be communicatively connected to, a database 240 or other data storage mechanism (e.g., one or more hard disk drives, optical storage drives, solid state storage devices, etc.). The database 240 may include data such as customer web profiles, product data, web page templates and/or web pages, and other data necessary to interact with the user 204 through the network 130. As discussed with reference to the controllers 155 and 170, it should be appreciated that although FIG. 1D depicts only one microprocessor 228, the controller 224 may include multiple microprocessors 228. Similarly, the memory of the controller 224 may include multiple RAMs 230 and multiple program memories 226. Although the FIG. depicts the I/O circuit 234 as a single block, the I/O circuit 234 may include a number of different types of I/O circuits. The controller 224 may implement the RAM(s) 230 and the program memories 226 as semiconductor memories, magnetically readable memories, and/or optically readable memories, for example.

In addition to being connected through the network 130 to the user devices 206-216, as depicted in FIG. 10, FIG. 1D illustrates that the web server 202 may also be connected through the network 130 to the central processing system 140 and/or one or more facility servers 126. As described below, connection to the central processing system 140 and/or to the one or more facility servers 126 facilitates both the express refill ordering process and the subsequent process of forwarding the order so that it can be filled for pickup by the customer.

The program memory 226 and/or the RAM 230 may store various applications for execution by the microprocessor 228. For example, an application 236 may provide a user interface to the server, which user interface may, for example, allow a network administrator to configure, troubleshoot, or test various aspects of the server's operation, or otherwise to access information thereon. A server application 238 operates to populate and transmit web pages to the web-enabled devices 206-216, receive information from the user 204 transmitted back to the server 202, and forward appropriate data to the central processing system 140 and the facility servers 126, as described below. Like the software 171, the server application 238 may be a single module 238 or a plurality of modules 238A, 238B. While the server application 238 is depicted in FIG. 1D as including two modules, 238A and 238B, the server application 238 may include any number of modules accomplishing tasks related to implantation of the web server 202. By way of example, the module 238A may populate and transmit the web pages and/or may receive and evaluate inputs from the user 204 to receive an express refill order, while the module 238B may communicate with one or more of the back end components 104 to fulfill the express refill order.

Typically, a patient or customer may launch or instantiate a user interface application (e.g., a web browser or other client application) from a web-enabled device, such as the web-enabled devices 206-216, to access the web server 202 cooperating with the system 140 to implement the express refill system 100. As used herein, the term "customer" may be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason or desire to refill one or more prescriptions, whether the prescriptions are related to a single patient or multiple patients. For example, a customer could be a caregiver responsible for patients with a specific disease that progresses in a known manner. The caregiver customer might greatly benefit from gaining information related to various medications and health products to assist in his or her caregiver responsibilities. In any event, while the term "customer" is used interchangeably with the term "patient," in this specification the term "customer" is used primarily so as to avoid confusion. Generally, the term "user" is used when referring to a person who is operating one of the web-enabled devices 206-216.

Also, as mentioned above, the pharmacy 112 may be any of the channels through which the entity implementing the express refill system 100 serves its pharmacy customers. Thus, the pharmacy 112 may be a retail pharmacy 112 in the customer's neighborhood (or any other drug store in a drug store chain), an on-line pharmacy or an on-line interface to a pharmacy 112 or to a retail network 110 (where the customer uses a web-browser to communicate with the server application 238, a phone/touch-tone interface to a pharmacy 112 or to a retail network 110 (where the customer uses a phone service to communicate with the server application 238), a mail-order pharmacy, a central-filling facility, a specialty pharmacy, or any other type of pharmacy affiliated with the entity implementing the express refill system 100.

In some embodiments, a pharmacist, other pharmacy staff, or a customer service representative (all referred to herein simply as "the pharmacist") invokes the express refill system 100 while interacting with a customer at a pharmacy 112 or over the telephone (e.g., from a retail pharmacy 112, or a call center). The pharmacist will have access to one of the pharmacy workstations 128 or to one of the web-enabled devices 114 and may invoke the express refill system 100. In other embodiments, the customer invokes the express refill system 100 (e.g., at a kiosk, via an Internet interface terminal at the pharmacy, etc.) by accessing the express refill system while physically present in a pharmacy 112.

As described above, one or both of the databases 146 and 182, illustrated in FIGS. 1A and 1B, respectively, include various information about the pharmacy's customers and the prescriptions filled by the pharmacy, as well as various business information including, but not limited to, information associated with third-party payors (e.g., insurance companies), employee information, and the like. Customer records are among the exemplary data that the system 100 may store on the databases 146 and 182. A customer record contains important information about the customer and the various pharmacy services that have been invoked by, or on behalf of, the customer in a customer profile. The customer profile includes basic biographical information about the customer, such as a customer name, a customer address, a customer phone number, an insurance carrier associated with the customer, an insurance group number for the customer, an insurance ID number for the customer, a customer birth date, a health history or condition, customer purchase history, etc.

The purchase history may include data related to purchases the customer routinely makes or has made at the pharmacies 110. For example, a customer may make purchases of several healthcare products such as OTC cold and flu symptom relievers, or may purchase or rent rehabilitative products such as crutches, a cane, a heating pad, bandages, etc. The purchase history data may include any product sold by the pharmacies 110 and purchased by a customer, whether in person or online. Where purchases are made by the customer in the store, the purchase data made be linked to the customer record though credit card, an in-store savings card, or other type of point-of-sale identification. Where the purchases are made by the customer over the network 130 or on-line, the purchases may be linked to the customer record through a web-based profile that is accessible by the customer through the web-enabled device 206-216, as herein described.

Additionally, the customer profile may include other information such as credit card information or other payment information, one or more customer e-mail addresses, user name and/or password information, online security question/answer information, etc. Of course, the customer record may also include other, more or less information than that described above.

The customer record also includes prescription data for each prescription filled by the pharmacy for the customer. The prescription data generally include, but are not limited to: a name of the medication; an indication whether a generic may be substituted; a dose (i.e., pills per day) of the medication; a number of days of medication to be dispensed (also referred to herein as a "day supply" or a "prescribed day supply"); a number of refills prescribed; a number of refills remaining; a prescription date; a prescribing physician; a phone number for the prescribing physician; a date on which the prescription was most recently adjudicated; a calculated date on which the prescription may next be adjudicated for the prescription; a remaining day supply for the prescription; a percent-consumption period indicating the number of days it would take to consume the required minimum percent-fill consumed of the fill for the prescription); and a prescription number. Of course, the prescription data need not include all of the information above, such as when the system 100 determines some information (e.g., the next adjudication date) but does not store it, or stores it some place other than with the prescription data in the database 146 or the database 182. Moreover, the prescription data may include additional information not mentioned above.

As described above, to access the express refill system 100 the customer 204 executes a client application on the web-enabled device 206-216 (e.g., by opening a web browser). Using the client application the user 204 may request and navigate a series of web pages transmitted, preferably in a secure manner (e.g., using Hypertext Transfer Protocol Secure, known as "HTTPS"), by the web server 202 to the web-enabled device 206-216. FIGS. 2-9 and 12A-12F depict web pages that the web server 202 may transmit in various embodiments of the express refill system 100. Some of the web pages share common elements. With reference to a "landing" web page 250 (i.e., the web page at which users "land" when they enter the pharmacy's domain name into their browser) depicted in FIG. 2, each of FIGS. 2-6 includes a store logo 252, a store locator link 254, a log in block 256, a navigation banner 258, a search bar 260, a shopping list link 262, and a shopping cart link 264. The navigation banner 258 allows users to navigate to different product areas (e.g., beauty, health & well being, home medical, etc.) of the virtual store and to access the store's various services (e.g., photo services, pharmacy services, clinic services, etc.).

It should be understood that it may be desirable for some or all of the data transmitted from the web server 202 to the web-enabled device 206-216, or vice versa, to be encrypted and/or otherwise transmitted in a secure manner.

Figure 2:
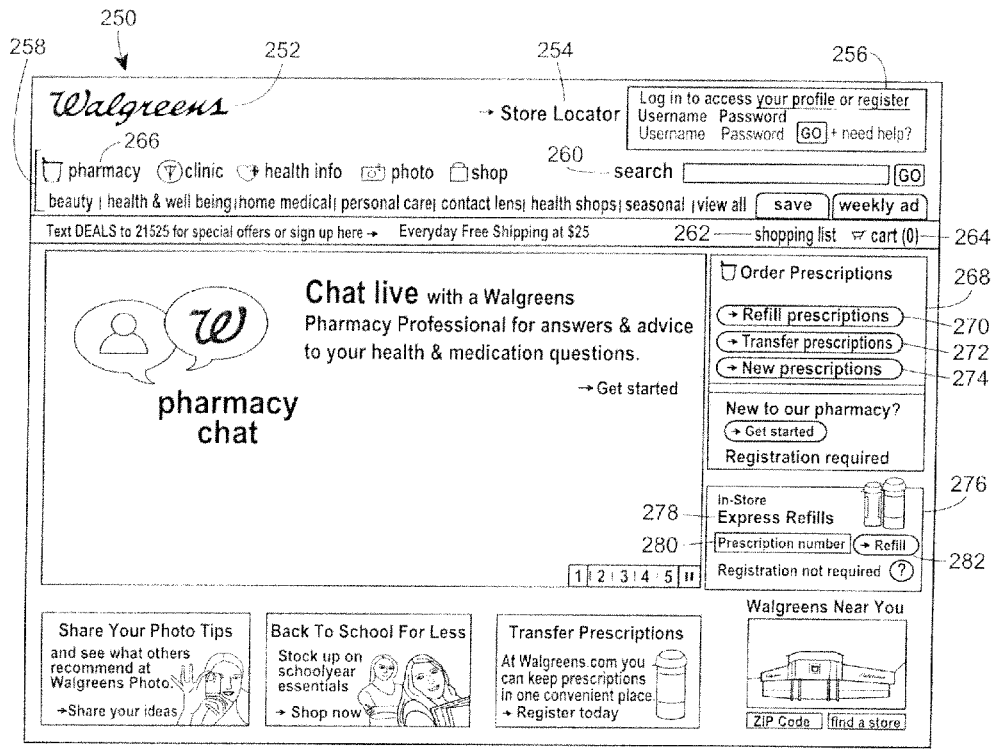
FIG. 2 depicts a landing web page transmitted by the web server of FIG. 1D.

The landing web page 250 depicted in FIG. 2 includes several links related to the store's pharmacy services. In addition to a "pharmacy" link 266 in the navigation banner 258, the landing web page 250 also includes an "Order Prescriptions" area 268 highlighting and providing direct access to specific pharmacy services. By clicking on one of links 270, 272, and 274, for example, users may access prescription refill services, prescription transfer services, and new prescription services, respectively. In some embodiments, accessing one or more of the refill, transfer, or new prescription services requires the user to register with and/or log into the web site by, for example, clicking on the "register" link in the log in block 256 or entering a username and password in the log in block 256 if the user is already registered.

In some embodiments, the landing web page 250 also includes an express refill area 276 that provides one or both of a link 278 to an express refill web page and an express refill field 280 that allows a user to enter a prescription number and, by clicking on a "refill" button 282, to place a prescription order through the express refill system 100.

Figure 3:
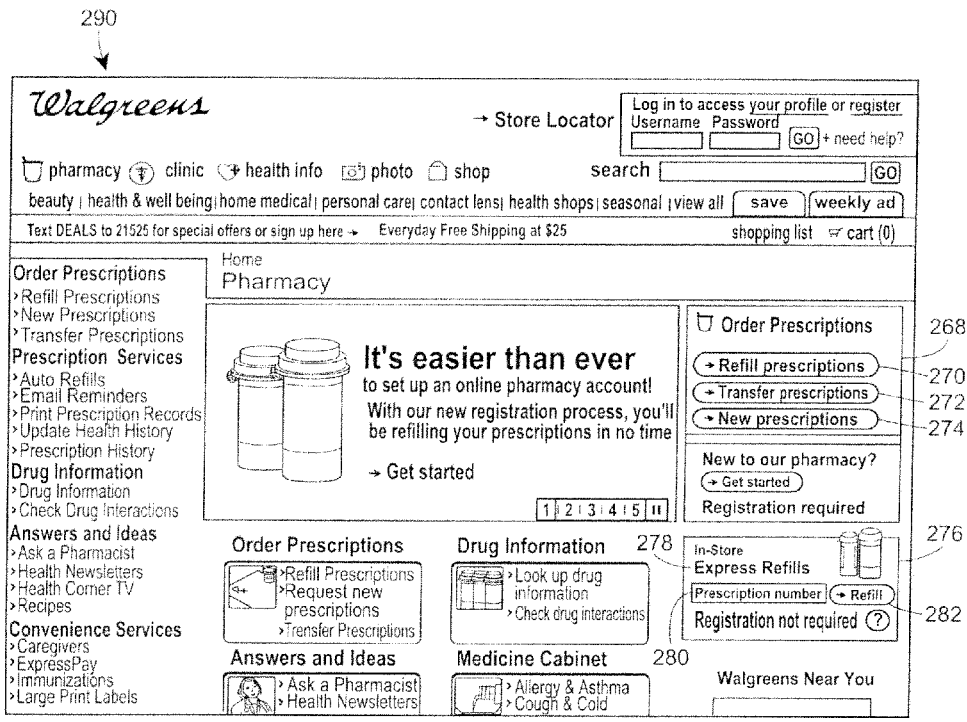
FIG. 3 depicts a pharmacy web page transmitted by the web server of FIG. 1D.

FIG. 3 illustrates a pharmacy web page 290 that the web server 202 may transmit to a web-enabled device 206-216 in response to the user 204 clicking on the pharmacy link 266. The pharmacy web page 290 includes links to pharmacy-related information, such as drug information, drug interactions, and health-related news and products, and to pharmacy services such as ordering prescriptions, viewing prescription records, and various convenience services such as setting up auto refills, electronic mail reminders, and the like. The pharmacy web page 290 also includes the Order Prescriptions area 268 and/or the express refill area 276.

Figure 4:
FIG. 4 depicts an express refill web page transmitted by the web server of FIG. 1D.

When a user clicks on the express refill link 278 illustrated FIGS. 2 and 3, the web server 202 receives the request and, in response, transmits an express refill web page 300, illustrated in FIG. 4. The express refill web page 300 includes a prescription number entry section 302 providing one or more fields 304 into which a user may enter prescription numbers for express refill. In the event that the fields 304 that are initially displayed on the express refill web page 300 are insufficient for the user, the user 204 may click an "add more prescriptions" link 306 to increase the number of fields 304 displayed. The number of fields 304 initially displayed, as well as the number of fields added in response to a user clicking the add more prescriptions link 306 and the maximum number of prescriptions that a user may enter at one time are selectable at the time that the web page 300 and the system 100 are programmed. However, in some embodiments, there are between one and five fields 304 provided initially, and the link 306 adds an additional one to five fields 304. Depending on the arrangement of the fields 304, it may be preferable in some embodiments to select the number of fields 304 such that all relevant information on the express refill web page 300 is displayed without requiring the user 204 to scroll the screen.

In some embodiments, an electronic mail address field 308 is also provided so that a user may enter an electronic mail address to which notifications regarding the prescriptions may be sent. The electronic mail address field 308 may be a required field or an optional field, depending on the proprietor's preference. If a user provides an electronic mail address, the express refill system may use the electronic mail address to notify the user that requested prescriptions are ready for pick up, that the pharmacy was unable to refill a prescription, and/or that the order was successfully placed.

A button 310, which may be labeled "continue" or "submit," for example, transmits the information entered into the fields 304 and the field 308 to the web server 202. The fields 304 into which prescription numbers are entered, in many embodiments, may accept prescription numbers related to a single patient or to multiple patients. By way of example, this flexibility allows a caregiver to refill prescriptions for multiple patients in the caregiver's charge or a family member to refill prescriptions for multiple family members.

Figure 5:
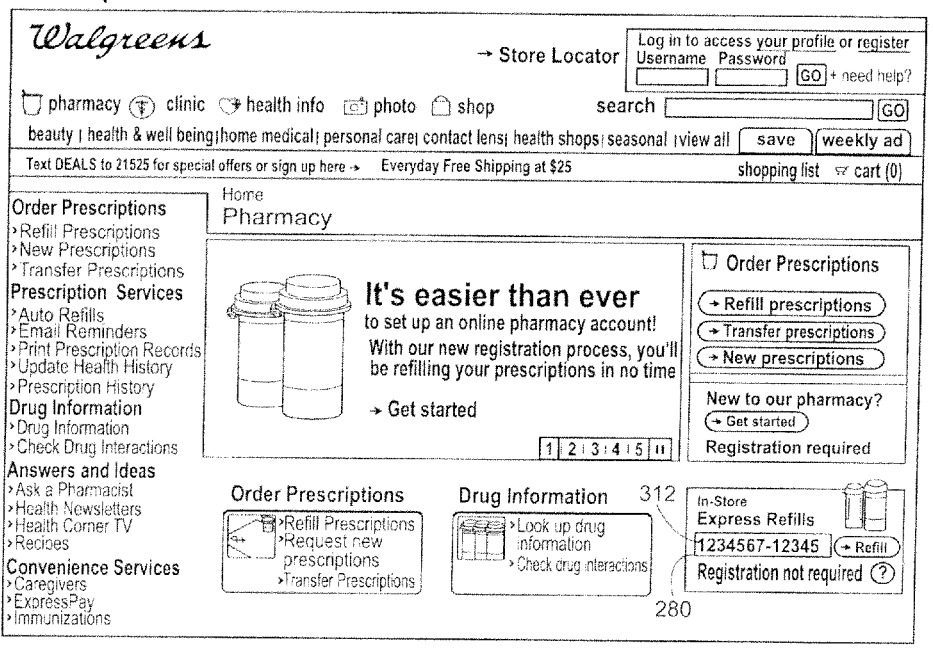
FIG. 5 depicts data entered into the pharmacy web page of FIG. 3.
Figure 9:
FIG. 9 depicts an order summary web page transmitted by the web server of FIG. 1D.

In some instances, a user viewing the web pages 250 or 290, illustrated in FIGS. 2 and 3, respectively, may enter a prescription number into the express refill field 280 and click on the refill button 282, instead of clicking on express refills link 278. FIG. 5 depicts the pharmacy web page 290 having a prescription number 312 entered into the express refill field 280. In some embodiments in which the user enters a prescription number into the express refill field 280, the web server 202 responds to a click on the refill button 282 in the same manner in which it would respond to a click on the continue button 310 on the express refill web page 300 (i.e., by proceeding with the express refill order, as described below). In other embodiments, however, the web server 202 responds to a click on the refill button 282 by transmitting the express refill web page 300 to the web-enabled device 206-216, and automatically entering the prescription number 312 (FIG. 5) into one of the fields 304, as illustrated in FIG. 6.

In any event, when the web server 202 receives the prescription numbers 312 entered by the user into the field or fields 304, the web server may issue a query to a database having a plurality of records corresponding to prescription numbers. The query may, in various implementations, be directed to the database 146, the database 182, or the database 240. In response to the query, the database may return results providing to the web server 202 information regarding whether each received prescription number is valid, the patient associated with the prescription, whether the prescription associated with each of the received prescription numbers has remaining refills, the store at which the prescription was last filled, the medication name, the medication strength, the drug quantity and/or day supply, etc.

Figure 7:
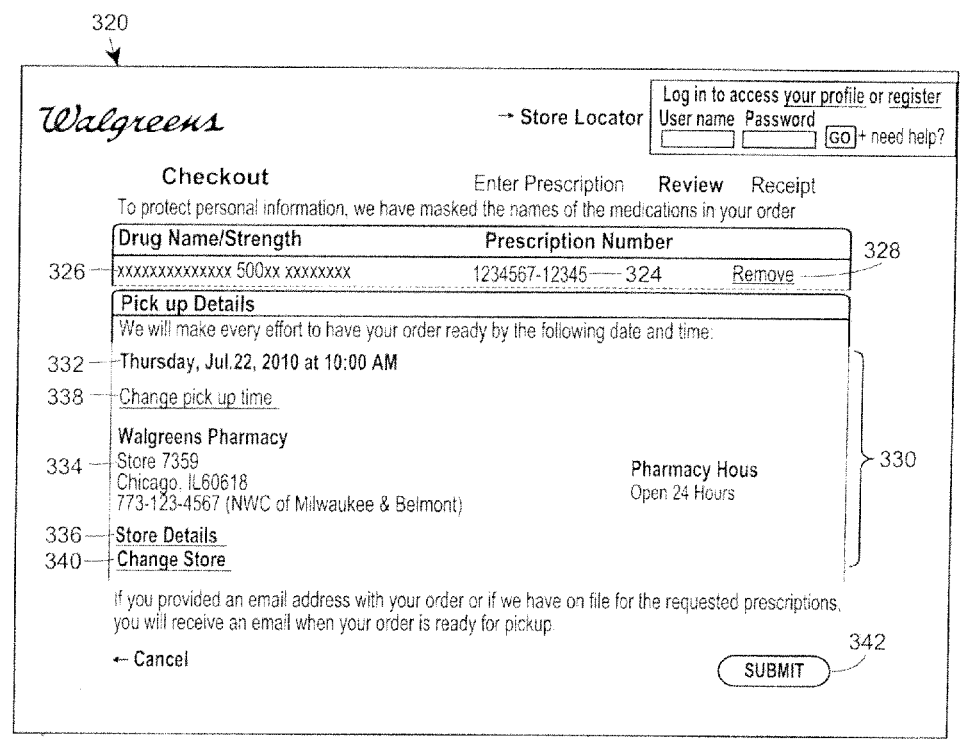

With reference now to FIG. 7, the web server 202, after receiving a query response from the database may transmit an order review web page 320 to the web-enabled device 206-216. The order review web page 320 includes a prescription information area 322 listing, for each prescription number received, the prescription number 324 and may also include information about the corresponding prescription medication such as the quantity, the medication name, the medication strength, the patient name, and the date on which the prescription was last filled. In the embodiment illustrated in FIG. 7, the prescription information area 322 includes the prescription number 324 and the corresponding drug name and strength 326. To protect patient privacy, some or all of certain fields may be masked. For example, the drug name and strength 326 may be masked but for a numerical portion of medication strength (i.e., "500"), as depicted in FIG. 7, or a patient name (e.g., "Joe Smith") may be masked but for one or two characters (e.g., Jxx Sxxxx). A "remove" link 328 next to each received prescription number 324 may allow the user to remove the prescription from the list of prescriptions requested for express refill.

The order review web page 320 may also include a pick up details area 330 that displays a pick up time 332 and a pickup store 334. A link 336 may allow the user to request additional details about the store, such as directions to the store, a map of the store location, store hours, store services, etc. Links 338 and 340, respectively, may allow the user to view a web page or a pop-up window (not shown) for changing the pickup time 332 and/or the pickup store 334. A submit button 342 allows the customer to finalize the order.

The express refill system 100 may determine the pickup store by any of several methods. Where the user submits only a single prescription number to the express refill system 100, the pickup store 334 may default to the store at which that prescription was last filled. The store at which the prescription was last filled may be determinable from the prescription number itself, for example, where some portion of the prescription specifies the store number. In the depicted embodiments, the prescription number (e.g., the store numbers 312, 324) specifies the store number 334 as the last 5 digits of the prescription number (i.e., "XXXXXXX-12345") or by a portion of the prescription number that falls after a delimiter (e.g., the portion after "-"). However, in other embodiments, the store number is determined according to information about the prescription number that is stored in one of the databases 146, 182, or 240. In the latter embodiments, the pickup store 334 may alternatively default to the last store at which any prescription associated with the patient was last filled. That is, the express refill system 100 could determine the patient associated with the received prescription number, and find the last store at which the patient picked up any of his medications.

Figure 8:
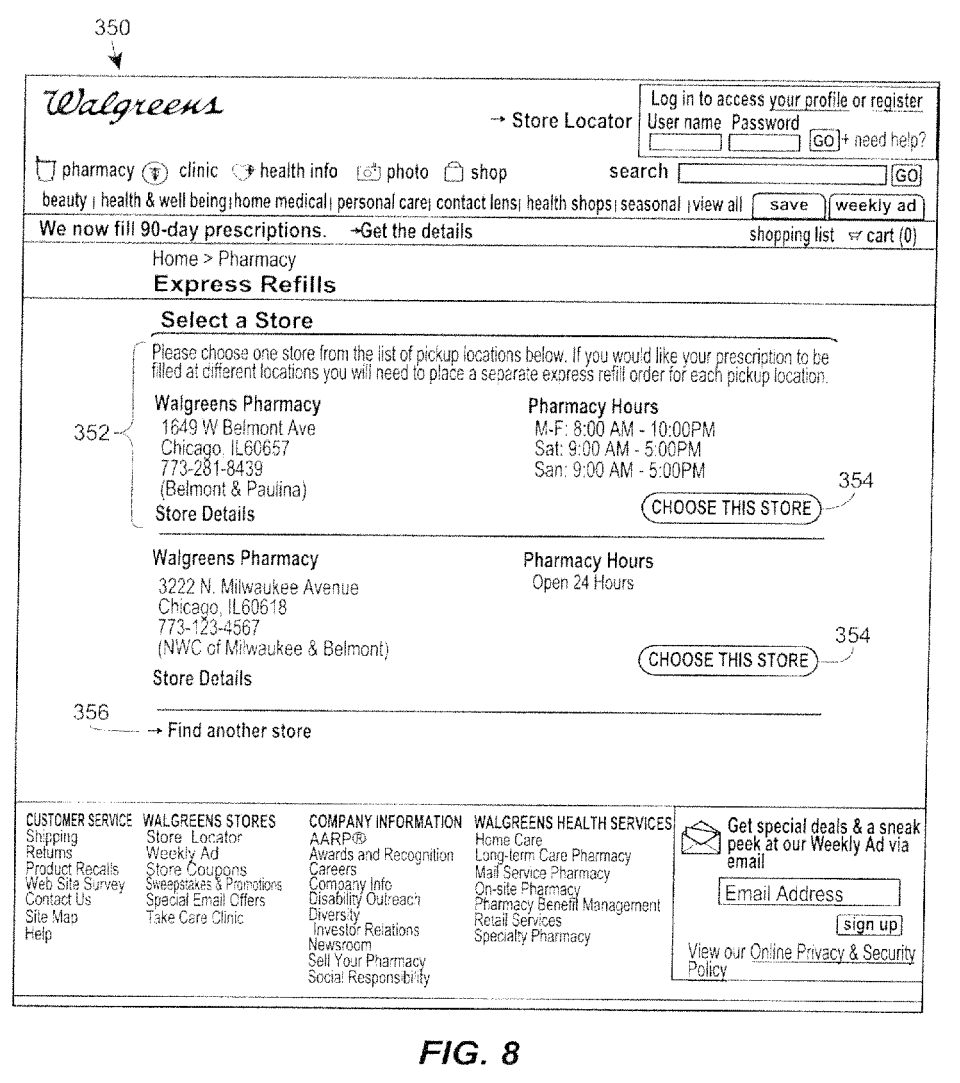

In any event, in embodiments in which a user may submit multiple prescription numbers at a time, the possibility exists that two or more of the prescriptions may have been filled most recently at different stores. In these instances, the pickup store 334 may similarly default to the store at which the most recently filled of the associated prescriptions was filled or the pickup store 334 may default to the store at which the most recently filled prescription associated with the patient or patients was filled. Alternatively, in some embodiments, the two or more stores associated with the prescription numbers received by the express refill system 100 may be displayed to the user and the user asked to specify a pickup store 334. FIG. 8 illustrates an exemplary store selection web page 350. The store selection web page 350 displays two or more store areas 352, each of which may display information about the store such as a store number, a store address, a store phone number, cross streets for the store, store hours, pharmacy hours, etc. Each store area 352 may have a button 354, labeled "choose this store," for example, by which the user may select a store at which to pick up the multiple prescriptions associated with the prescription numbers the user submitted. The store selection web page 350 may also include a link 356 to allow the user to find another store at which to pick up the multiple prescriptions.

Once a user has reviewed the order review web page 320 and is satisfied with the selected prescription numbers, the pickup time 332, and the pickup store 334, the user may click on the submit button 342. Upon receiving an indication that the user has clicked on the submit button 342, the web server 202 transmits an order summary web page, such as the exemplary order summary web page 360 illustrated in FIG. 9. Like the order review web page 320, the order summary web page 360 includes a prescription information area 362 and a pickup details area 364. A button 366 may allow the user to print the order summary web page 360.

FIG. 10 depicts an overview 370 of an express refill method performed by the express refill system 100. Generally speaking, the express refill method begins by transmitting (from the web server 202) a web page (e.g., web pages 250, 290, 300) including at least one prescription number entry field (e.g., the fields 280, 304) (block 372). After a user enters one or more prescription numbers (e.g., the prescription number 312) into the prescription number entry field(s), and clicks on a button (e.g., buttons 282, 310) to submit the one or more prescription numbers, the express refill system 100 and, in particular, the web server 202, receives the prescription numbers (block 374). In some embodiments, the express refill system 100 validates the prescription numbers received (step 376), as described in more detail below. Thereafter, the express refill system 100 determines a refill retail location (i.e., a pickup store) (block 378). The web server 202 then transmits an order review web page (e.g., the web page 320) (block 380) and waits until it receives an indication that the customer has confirmed the order (block 382). Having received the order confirmation, the web server 202 may transmit an order summary web page (e.g., the web page 350) (block 384).

Figure 11:
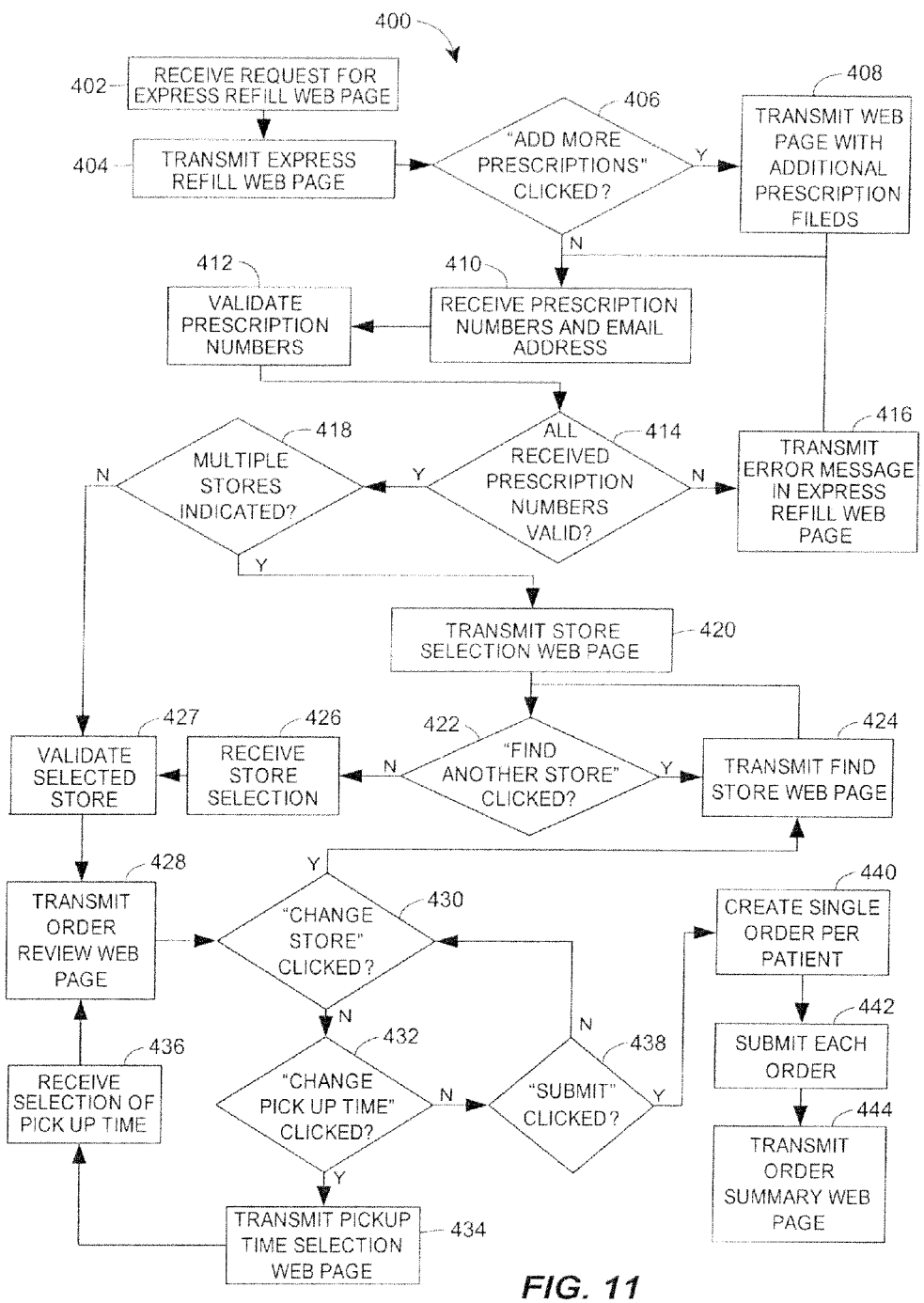
FIG. 11 illustrates an exemplary detailed method implementing the express refill system in accordance with the presently described embodiments.

The method 400 illustrated in FIG. 11 provides additional detail about the method executed by the express refill system 100. In one of the various manners described above, a customer may enter the express refill system 100 by, for example, entering the pharmacy domain name into a web browser and clicking on the express refills link 278 on the landing web page 250. Of course, the user could alternatively enter the express refill system 100 by navigating from the landing web page 250 to the pharmacy web page 290 (e.g., by clicking on the pharmacy link 266), and then clicking on the express refills link 278 on the pharmacy web page 290, or by entering a prescription number 312 into the express refill field 280 on either the landing web page 250 or the pharmacy web page 290.

In any event, upon receiving a request for the express refill web page 300 (block 402), the web server 202 transmits the express refill web page 300 over the network 130 for display on the web-enabled device 206-216 (block 404). If the user clicks the "add more prescriptions" button 306 (block 406), the web server 202 may retransmit the express refill web page 300 with additional fields 304, and may optionally include any prescription numbers 312 already entered into the fields 304. When the user clicks on the continue button 310 (presumably after the user is finished entering prescription numbers 312 into the fields 304) the prescription numbers 312 are transmitted to the web server 202. If the user has entered an electronic mail address into the field 308, the electronic mail address is also captured and transmitted to the web server 202. Of course, because some embodiments of the express refill system 100 do not require the user to log into the system, the electronic mail address may be stored with the order so that the user can be notified when the order is ready.

Having received the prescription numbers 312 and, optionally, the electronic mail address (block 410), the web server 202 may proceed to validate the received prescription numbers 312 and electronic mail address (block 412). Validation of the prescription numbers 312 may include one process or multiple steps. In various embodiments, the web server 202 may check the length of each prescription number 312 (e.g., to determine whether it is the right length), determine whether the prescription number 312 includes any unacceptable characters (e.g., special characters, non-numeric characters, etc.), determine whether each prescription number 312 includes a delimiter (e.g., a hyphen or a space), and/or determine whether the prescription number 312 indicates a pickup store 334 and, if so, if the indicated pickup store 334 is valid. Whether an indicated pickup store is valid may be based on the type of store indicated in some embodiments (e.g., in some instances mail order stores may not be valid) or whether the prescription in question has been previously filled at the indicated store. Of course, while some embodiments may validate the received prescription numbers 312 in each of these manners, other embodiments may skip the validation step entirely, may perform validation later in the express refill process, or validate the prescription numbers 312 according to some combination of these manners. While the validation process is described as performed by the web server 202, it should be understood that one or more portions of the validation process may occur in the web-enabled user device 206-216, such as when computer-executable instructions (e.g, JAVA, JAVAscript, etc.) are transmitted as part of the web page 300. Further, in some embodiments, the web server 202 (or the computer-executable instructions transmitted as part of the web page 300) may perform validation on an electronic mail address if the user enters an electronic mail address into the field 308 (e.g., to verify that it includes at least '@' and '.' characters.

Validation of the received prescription numbers 312 (block 412) may also include validating each prescription number 312 against a database of prescription numbers (e.g., in one of the databases 146, 182, or 240). If the express refill system 100 determines that one or more of the received prescription numbers 312 are invalid (block 414) (e.g., wrong format, not enough characters, invalid prescription number, etc.), the web server 202 may retransmit the express refill web page 300 with an error message included (block 416), and the web server 202 may again wait to receive prescription numbers (block 410). If, instead, the system 100 determines that all of the received prescription numbers 312 are valid, the system 100 proceeds to determine whether the received prescription numbers 312 indicate (or are associated with) multiple stores (block 418). Of course, if the web server 202 receives only one prescription number, only one store will be indicated.

If, on the other hand, the web server 202 received multiple prescription numbers 312 from the user, and if the multiple prescription numbers 312 indicate (or are associated with) multiple stores, the web server 202 may transmit a store selection web page (e.g., the web page 350) or, in some embodiments, may assume or default to one of the indicated (or associated) stores, or even a different store, as described above with reference to FIG. 7.

If the web server 202 transmits the store selection web page 350 (block 420), the next input the web server 202 receives from the user may be an indication that the user clicked on the "find another store" link 356 (block 422), in response to which the web server 202 may transmit a "find a store" web page (block 424), allowing the user to input an address or zip code and to find stores in a given vicinity. Alternatively, if the user clicks on one of the "choose this store" links 354, the web server 202 may receive a pickup store selection (block 426).

Upon receiving the pickup store selection (block 426) or determining that only a single store was indicated (block 418), the web server 202 may, in some embodiments, contact a server at the selected store (e.g., the facility server 126) to verify that the store can refill the prescription (block 427), considering current inventory, regulatory issues, pharmacy load, and/or any other factor that could prevent the prescription from being filled at that location. Of course, if the selected store cannot fill the prescription, the web server 202 may transmit an error message to that effect and may return the user to the find store web page. Otherwise, the web server 202 may transmit an order review web page (block 428), such as the order review web page 320.

As described above, the order review web page 320 may include links including a change store link 340, a change pickup time link 338, and a submit button 342. The web server 202 will respond according to the inputs received from the user. For example, if the user clicks on the "change store" link 340 (block 430), the web server 202 may transmit the "find a store" web page (block 424). Alternatively, if the user clicks on the "change pickup time" link 338 (block 432), the web server 202 may transmit a pickup time selection web page (block 434) and, in response to which the user may select a new pickup time (block 436). In any event, if the user opts to change the pickup store (block 430) or to change the pickup time (block 432), the method returns the user to the order review web page 320 (block 428) after the web server 202 receives the corresponding input (i.e., a store selection and/or a pickup time selection) from the user.

Once the user clicks on the submit button 342 (block 438) the web server 202 may, depending on the particular implementation of the system, perform one or more of several steps. In the implementation depicted by the method of FIG. 11, the web server 202, upon receiving an indication that the user has clicked the submit button 342 (block 438), may create an order for the patient (block 440). As described above, in some embodiments, the express refill system 100 may receive prescription numbers 312 associated with more than a single patient. For example, a person may submit refills for a spouse and/or children through the express refill system 100. In such embodiments, the web server 202 may create a single order or may create one order for each patient associated with a received prescription. In any event, the web server 202 may then submit the order or orders (block 442) created to the designated pickup store 334, to a central database handling prescription processing, to prescription handling routine, to a prescription processing system, or to any routine or system otherwise appropriately routing the prescription orders. The web server 202 may then transmit an order summary web page for display to the user (block 444) such as the order summary web page 360 illustrated in FIG. 9.

Of course, various embodiments of the express refill system 100 may include or omit one or more of the web pages 250, 290, 300, 320, 350, and 360, according to the specific preferences of the proprietor. Likewise, various elements of the methods 370 and 400 depicted in FIGS. 10 and 11 may be executed at different times, and some elements may be omitted entirely. Additionally, it should be understood that each of the actions and/or decisions depicted as included in the methods 370 and 400 may include a corresponding action in another device. For example, each transmission of information is, presumably, accompanied by a corresponding receipt of that information at another device, and vice versa. It should also be understood that the for each step performed by the web-enabled devices 206-216, the web server 202, or any other device in the express refill system 100, (e.g., for any transmission step, receipt step, display step, storage step, decision step, determination step, etc.,) corresponding machine-readable instructions are stored in a memory for execution by a processor to perform the step.

When the prescription order has been filled, and is ready at the designated pickup store 334, the pharmacy (or a system operated by the pharmacy) may transmit a notification to the customer to inform the customer that the prescription order is ready for pickup. The notification may be by telephone, by short message service (SMS), by electronic mail, or by some combination of the above. In instances where the customer provided an electronic mail address in the electronic mail address field 308, a notification may be generated and transmitted to the electronic mail address received by the web server 202. In some embodiments, a notification may be transmitted for each order. For example, if prescriptions numbers for three patients are received, the system 100 groups them into three orders and sends three notifications. In instances where the customer did not provide an electronic mail address in the electronic mail address field 308, a similar notification or notifications may be transmitted to the electronic mail address (or addresses) associated with patient profiles corresponding to the received prescription numbers 312. If the customer did not provide an electronic mail address in the electronic mail address field 308 and no electronic mail address is associated with a profile corresponding to a particular patient, no notification will be transmitted.

It should be appreciated that the methods 370 and 400 depicted in FIGS. 10 and 11, respectively, do not include any mention of the user logging into the system 100. In contrast to other prescription services that may be provided by the pharmacy 112, such as refilling prescriptions by selecting from a history of prescriptions, or adding or transferring a prescription, the express refill system 100 does not require access to a user profile and, therefore, the user is freed from the necessity of inputting and submitting a username and password. For users who are not yet registered with the online store, and do not have a user profile, the users are freed from having to complete the registration and profile creation processes prior to refilling one or more prescriptions.

While the description above relates primarily to embodiments in which the customer will pick up the prescriptions ordered via the express refill system 100, other embodiments are contemplated in which the express refill system 100 may also interoperate with a prescription mail delivery system and/or a prescription mail delivery service, which may be associated with the retail network 110 or may operate as a separate service. For example a store number embedded in the prescription number or otherwise associated with a prescription number may indicate that the prescription was last filled by mail order, and the express refill system 100 may treat the prescription accordingly. In some embodiments, the express refill system 100 may confirm a recipient address instead of a pickup store, and may prevent the customer from changing the pickup address from that currently associated with the prescription. Of course, where multiple prescription numbers 312 are received and multiple addresses are associated with the prescription numbers, the express refill system 100 may decline to process the order and instead require the customer to log into the store web site or place the order in person or by phone.

The ease with which a customer can place orders to refill prescriptions through the express refill system 100 described herein makes it particularly suitable for mobile customers. In fact, the minimal input required by the customer makes the express refill system 100 extremely versatile. Embodiments of the systems and methods described above are contemplated in which the express refill system 100 is implemented in a minimalistic interface suited for a web-enabled mobile phone, smart phone, personal digital assistant, etc., or in an application for execution on such a device. For example, an application for a mobile device (e.g., the web-enabled devices 206-212) may be developed for a mobile platform such as the Android™, Palm® webOS, or iOS® mobile technology platforms, developed by Google Inc., Palm, Inc. (now Hewlett-Packard Company), and Apple, respectively. Accordingly, the application may interact with the express refill web server 202 described above. Additionally or alternatively, the application may interact with a server specially implemented and/or designated to provide the express refill service in cooperation with the application. Moreover, an application designed specifically to interact with the express refill system 100 may provide the field 308 for entering an email address (e.g., as depicted in FIG. 12C) or, alternatively, may transmit to the web server 202 (or other server) a stored email address that the user has associated with the mobile device. As another option, the application could transmit a phone number associated with the device, an application ID specific to the application instance operating on the mobile device, or other data (e.g., an internet protocol ("IP") address or a media access control ("MAC") address) associated specifically with the mobile device. Accordingly, the express refill system 100 may send one or more notification messages when the prescription or prescriptions are ready to be picked up. The notification may be transmitted to the email address entered by the user, to the email address transmitted automatically from the mobile device, to the mobile device as a text message, to the application as a notification or message displayed within the application, etc.

FIGS. 12A-12F depict various displays associated with an embodiment of the express refill system 100 implemented with a minimalistic interface such as, for example, a mobile-specific web site or a mobile device application. Mobile-specific web sites may used pared-down versions of HTML web pages, or may implement other "lightweight" web pages written in languages including Extensible Hypertext Markup Language (XHTML) or Wireless Markup Language (WML). The FIGS. 12A-12F include many of the same elements as described above with respect to FIGS. 2-9 and, just as described above, a customer using the interface depicted in FIGS. 12A-12F can complete an order to refill a prescription with as little as three inputs into two web pages. That is, if the customer navigates directly to a page having a prescription number field the customer may (1) enter a prescription number, (2) click the continue button, and (3) click the submit button after reviewing the order.

In embodiments implementing a mobile device application, the mobile device includes a processor and a memory. The application may be implemented as a series of machine-readable instructions for performing the various tasks associated with receiving information at, displaying information on, and transmitting information from the web-enabled device 206-212. Of course, the application itself may, at various times, be stored on the web-enabled device 206-212, a server (not shown) from which users download the application to a mobile device, a compact disc, a DVD, etc.

In some embodiments of the express refill system 100 implementing the mobile device application on a mobile device 206-216, the mobile device 206-216 includes an image capture device (not shown). The image capture device may be used by the application to capture an image of a barcode. Throughout this application the use of the word "barcode" is intended to be generic and inclusive of all types of barcodes. Barcodes could be, for example, the conventional rectangular segment barcodes as well as two dimensional QR codes or matrix barcodes. Most QR codes have black modules arranged in a square pattern on a white background. Smaller versions may be referred to as micro QR codes and design QR codes include a picture or logo to enhance conversion rates. In some embodiments, the mobile device application may interpret the captured barcode image to generate prescription data (such as a prescription number) and transmit the prescription data to the server 202. In other embodiments, the mobile device application may transmit the barcode image to the server 202, which may interpret the barcode image to obtain prescription data. In still other embodiments, the mobile device application may transmit the barcode image to a third-party server (not shown) which may interpret the barcode image to obtain prescription data and transmit the obtained prescription data to the server 202.

Figure 13:
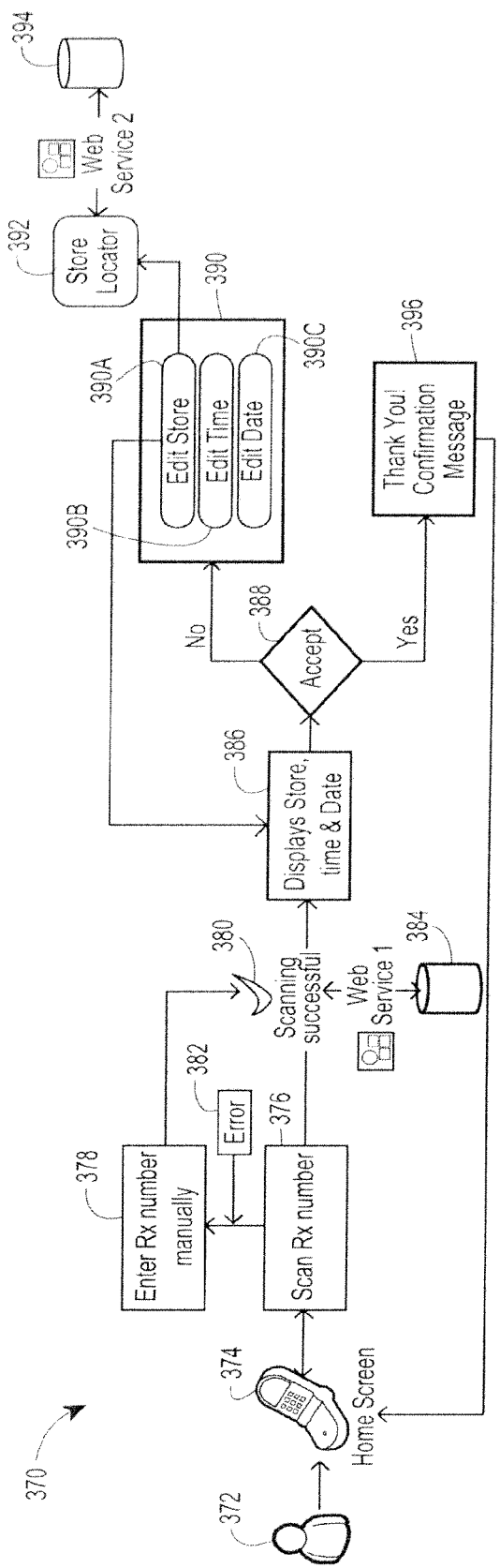
FIG. 13 illustrates an exemplary execution flow of an implementation of the express refill system using a mobile device application in accordance with the presently described embodiments.

FIG. 13 depicts an exemplary process flow 370 of an implementation of a mobile device application implementing the express refill system 100. A user 372 executes the application on the mobile device 374 to display a home screen of the application. The user selects to refill a prescription and the application displays a prescription scanning screen and activates an image capture device (i.e., a camera). The user 372 scans a barcode (376) to determine the prescription number by aligning the camera with a barcode on a receipt or container associated with a previously filled prescription, so that the barcode appears in an area of the screen. The mobile device application, in some embodiments, may automatically recognize that a barcode is present in the view of the image capture device, and may act automatically to capture and/or interpret the barcode. In other embodiments, the mobile device may require the user 372 to cause the image capture device to capture an image, before the mobile application interprets or otherwise uses the barcode image.

In any event, assuming that the barcode is captured successfully 380, the mobile device application may transmit the prescription number associated with the barcode to a server 384. In alternate embodiments, the mobile device application may transmit the captured barcode image to the server 384 and the server 384 may interpret the barcode image. In still other embodiments, the mobile device application may transmit the captured barcode image to a third-party server (not shown) and the third party server may interpret the barcode image and transmit a prescription number to the server 384 or back to the mobile device application for transmission to the server 384.

The server 384 may also retrieve records associated with the prescription number encoded by the barcode, including, by way of example and not limitation, a store at which a prescription associated with the prescription number was last filled, and a default time and date at which the user may pick up the refilled prescription. In the event that the barcode is not scanned successfully or the prescription is invalid or not available using express refill, an appropriate error message 382 may be displayed to the user 372.

Once the server 384 has determined the necessary information (prescription number, pickup store, default time and date, etc.) associated with the barcode, the mobile device application displays (386) the default pickup store, and the default time and date of pickup, on the device 374. The user 372 may select from a plurality of controls 390, including a control 390A to edit the store, a control 390B to edit the pickup time, and a control 390C to edit the pickup date. If the user 372 selects the edit store control 390A, the application may execute a store locator service 392 which may cooperate with a store location database 394 to allow the user 372 to select a pickup store. If the user 372 accepts (388) the information displayed at 386 (e.g., by selecting a "submit" button), the mobile device application displays a confirmation message 396, and returns the user to the home screen.

Figure 14A:
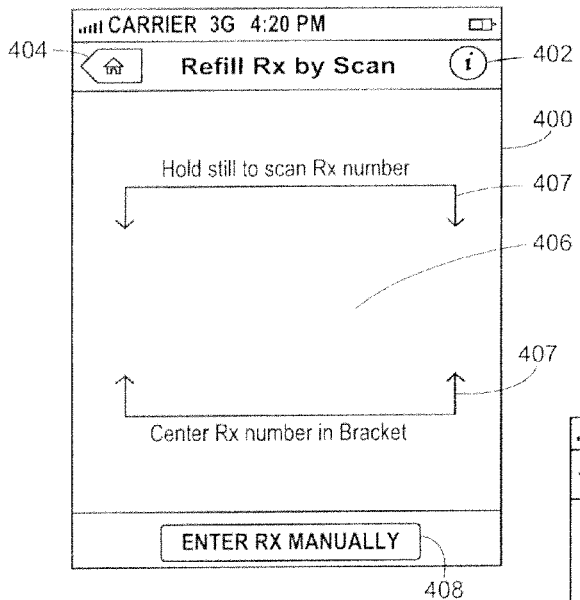
FIG. 14A depicts an image capture screen of a mobile device application in accordance with the presently described embodiments.

The various screens of the mobile device application, referred to above, are depicted in FIGS. 14A-K. FIG. 14A depicts an image capture screen 400 that may be displayed by the mobile device application. The image capture screen 400 may include an information button 402 that causes the mobile device application to display instructions associated with the express refill system 100, or causes a web browser of the mobile device to navigate to a web page containing such instructions. A home button 404 may cause the mobile device application to return to a home screen (not shown).

Figure 14B:
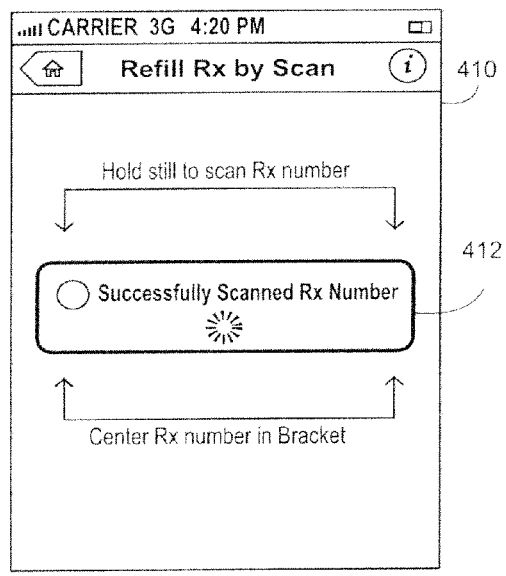
FIG. 14B depicts a screen indicating successful capture of an image in accordance with the presently described embodiments.

The image capture screen 400 also includes an image capture area 406, which may include an image capture frame indicated by marks 407 on the display. Aligning the prescription barcode within the marks 407 indicating the image capture frame may cause the application to capture and/or interpret the barcode. Alternatively, a button (not shown), when activated by a user, may cause the image capture device to capture the barcode image. A button 408 allows the user to input a prescription number manually, instead of capturing an associated barcode. If the barcode is captured successfully, the mobile device application may display a screen 410 with a success message 412, as depicted in FIG. 14B.

Figure 14C:
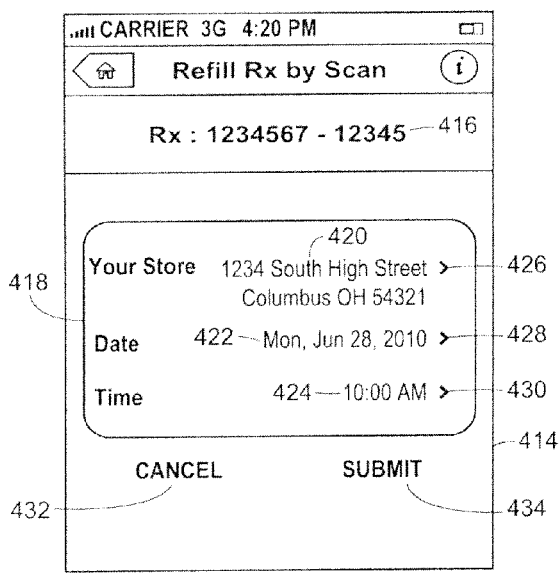
FIG. 14C depicts an order review screen of a mobile device application in accordance with the presently described embodiments.

Having transmitted the prescription number (or image) to the server, the mobile device application receives information back from the server indicating the default pickup store and default pickup time and date. This information may be displayed by the mobile device application in an order review screen 414, as depicted in FIG. 14C. As FIG. 14C illustrates, the order review screen 414 may display the prescription number 416 and order information 418. The order information 418 may include the pickup store 420, the pickup date 422, and the pickup time 424. Each of the pickup store 420, the pickup date 422, and the pickup time 424 may have an associated control 426, 428, and 430, respectively, that allows the user to change the corresponding item, as described below. A cancel button 432 may allow the user to cancel the process and return to the home screen, while a submit button 434 allows the user to submit the prescription refill order.

In some embodiments, the control 426 that allows the user to change the selected store may activate—or give the user an option to activate—a geolocation device (e.g., a global positioning system (GPS) device) in the web-enabled device 206-216, particularly if the device is a mobile device (e.g., the devices 206-214). The geolocation device may, by itself or cooperating with another application or an online service, provide the mobile device application with an indication of the mobile web-enabled device's current position, which the mobile device application may use to determine the closest store at which the requested prescriptions can be filled.

Figure 14D:
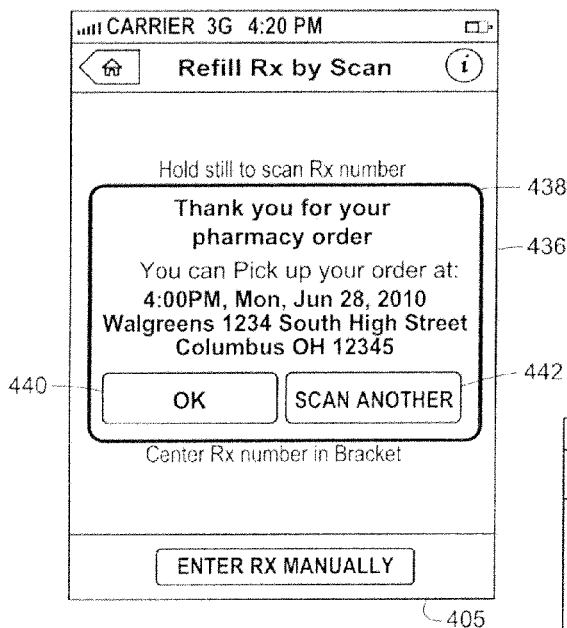
FIG. 14D depicts an order summary screen of a mobile device application in accordance with the presently described embodiments.

If the user activates the submit button 434, the mobile device application may display an order confirmation screen 436, such as that depicted in FIG. 14D. The order confirmation screen 436 may include an order confirmation message 438. Buttons 440 and 442 may, respectively, allow the user to return to the home screen or to scan another barcode. An additional button (not shown) may cause a calendar entry or other reminder to be stored in another application (e.g., a calendar application) on the mobile device.

Figure 14E:
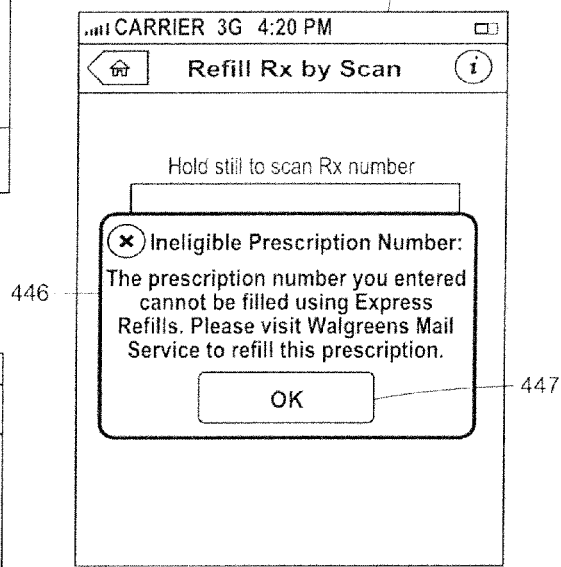
FIG. 14E depicts an error message screen of a mobile device application in accordance with the presently described embodiments.

FIG. 14E depicts an error message 446 that the mobile device application may display on an error screen 444. A button 447 allows a user to dismiss the message.

Figure 14F:
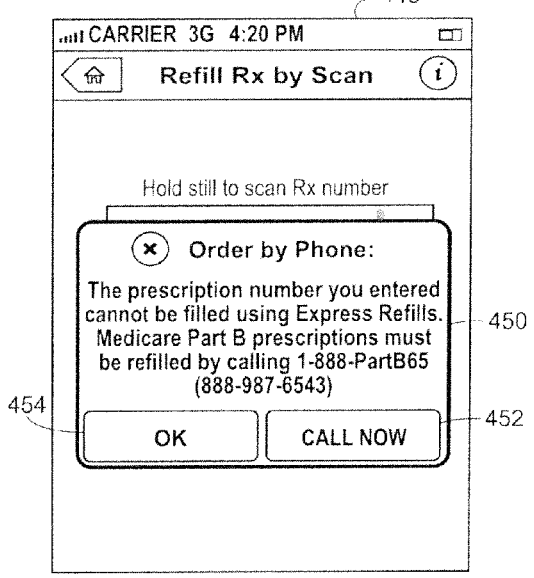
FIG. 14F depicts a second error message screen of a mobile device application in accordance with the presently described embodiments.

FIG. 14F depicts a second embodiment of an error message displayed by the mobile device application. Specifically, an error screen 448 depicts an error message 450 directing the user to order the requested prescription by phone. A button 452 may cause the mobile device, if it is a mobile telephone, to dial the number displayed. A button 454 may allow the user to dismiss the error message.

If the user activates the control 424 (FIG. 14C), the mobile device application may display a screen 456 to allow the user to select and/or request a new pickup time. The screen 456 may include a pick list 458 from which the user may select a time 460 to pick up the refilled prescription. Of course, other input means may be used, such as numeric entry fields, radio buttons, etc. When the user has made a selection, the user may activate a button 462 to accept the choice and return to the order review screen 414. Alternatively, the user may activate a cancel button 464 to cancel the request to change the pickup time and return to the order review screen 414.

Similarly, if the user activates the control 422 (FIG. 14C), the mobile device application may display a screen 466 to allow the user to select and/or request a new pickup date. The screen 466 may include a pick list 468 from which the user may select a date 470 on which to pick up the refilled prescription. Of course, other input means may be used, such as numeric entry fields, radio buttons, etc. When the user has made a selection, the user may activate a button 472 to accept the choice and return to the order review screen 414. Alternatively, the user may activate a cancel button 474 to cancel the request to change the pickup time and return to the order review screen 414.

Figures 14G, 14H, 14I:
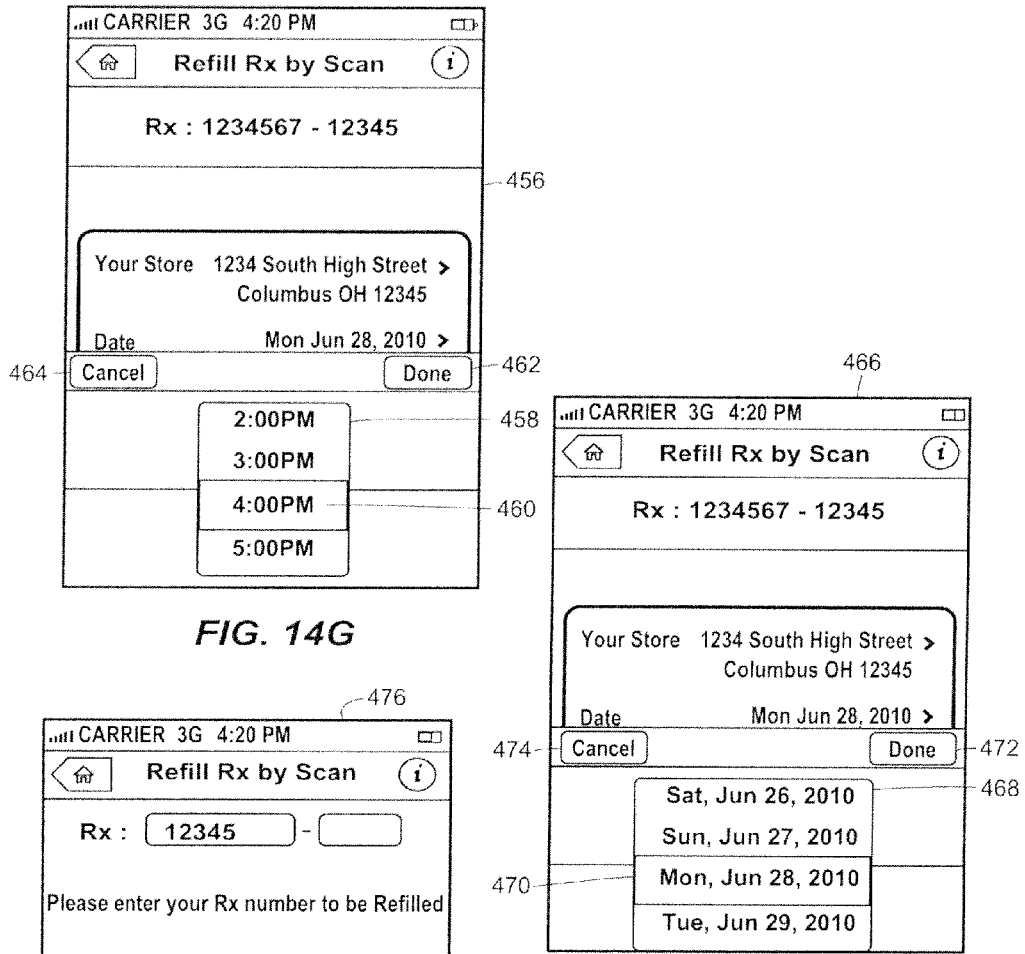
FIG. 14G depicts a pickup time selection screen of a mobile device application in accordance with the presently described embodiments.
FIG. 14H depicts a pickup date selection screen of a mobile device application in accordance with the presently described embodiments.
FIG. 14I depicts a manual prescription number entry screen of a mobile device application in accordance with the presently described embodiments.
Figure 14J:
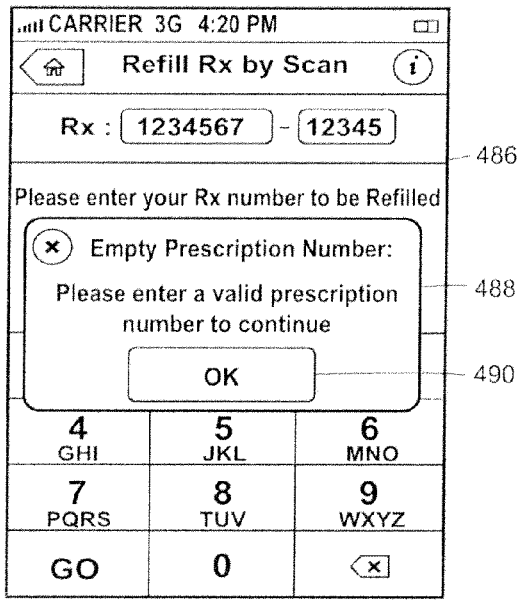
FIG. 14J depicts a first error message screen associated with the manual prescription number entry screen depicted in FIG. 14I.
Figure 14K:
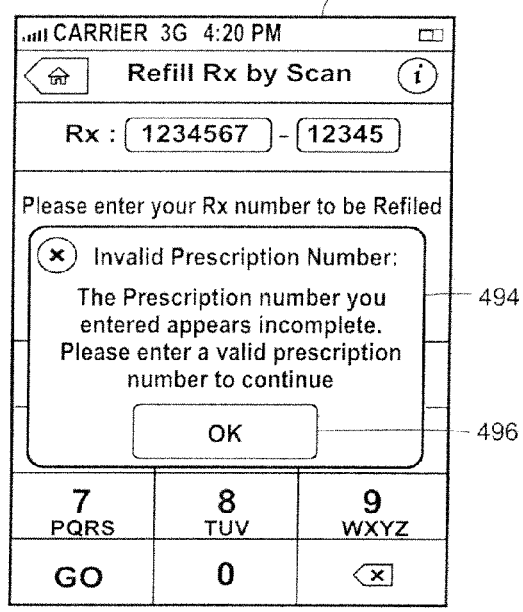
FIG. 14K depicts a second error message screen associated with the manual prescription number entry screen of FIG. 14I.

A screen 476, depicted in FIG. 14I, may allow a user to manually input a prescription number to submit to the express refill service if the user activates the button 408 illustrated in FIG. 14A. The screen 476 may include a numeric (or alpha-numeric) keypad 478 to allow the user to enter a prescription number into a prescription number field 480. A backspace key 482 may allow the user to delete one or more improperly entered characters, while a button 484 may allow the user to submit the entered prescription number.

The mobile device application may display error message screens 486, 492 (depicted in FIGS. 14J, 14K, respectively) if the user activated the button 484 while the prescription number field 480 in empty (i.e., null) (e.g., error message 488) or if the prescription number entered by the user in the field 480 is not a valid prescription number (e.g., error message 494). Buttons 490, 496 may allow the user to dismiss the respective error messages and return to the manual entry screen 476.

Figure 15:
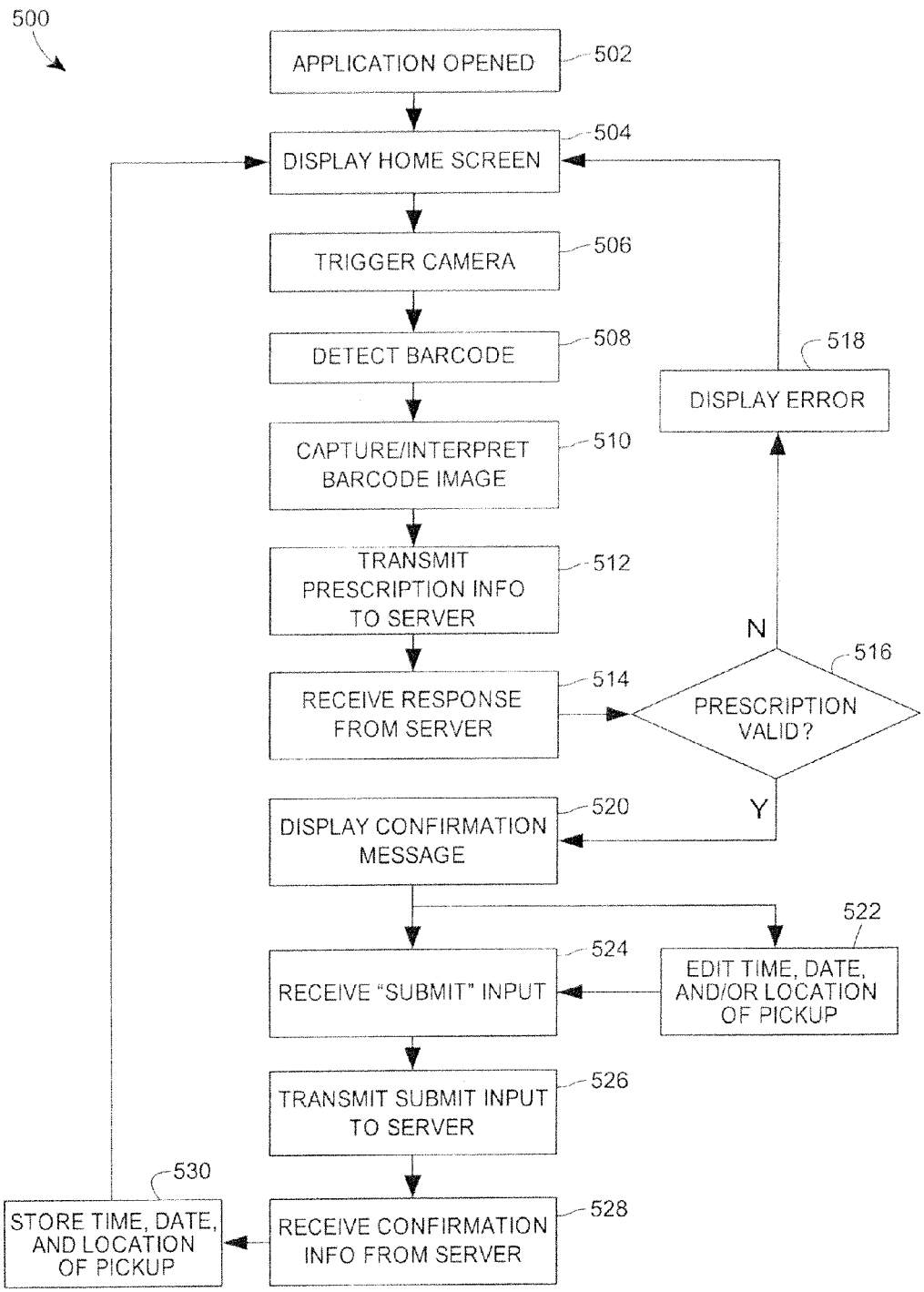
FIG. 15 depicts an exemplary method of implementing the mobile device application in accordance with the presently described embodiments.

FIG. 15 depicts a method 500 for implementing the express refill service using a mobile device application. The user executes the application (block 502) on the mobile device, causing the mobile device application to display a home screen (block 504). From the home screen, the user may select to refill a prescription using the express refill service or, alternatively, the application may assume the express refill functionality as the home screen. In any event, activation of the express refill service triggers the image capture device (block 506). The mobile device application may automatically detect the barcode (block 508) when the barcode is within the view of the image capture device. The mobile device application thereafter captures and/or interprets the barcode image (block 510) and transmits prescription data— which may be a prescription number or the barcode image— to the server (block 512). The server may interpret the prescription data and send a response to the mobile device application (block 514). If the response indicates that the prescription data is invalid, the mobile device application may display an error (block 518) and return to the home screen (block 504). If the prescription data is valid, the mobile device application may display a confirmation message (block 520), such as the order review screen 414 depicted in FIG. 14C. The user may edit the time and/or date at which the prescription will be ready to be picked up, and/or may edit the location at which the prescription will be refilled (block 522). Once the user has done so, or if the user does not do so, the mobile device application receives a "submit" input (block 524), which causes the mobile device application to transmit the "submit" input to the server (block 526). When the refill order has been placed, the mobile device application receives and displays confirmation information from the server (block 528), for example, in the screen 436 depicted in FIG. 14D. The mobile device application may also store the selected pickup time, date, and location (block 530), before returning the user to the home screen (block 504).

Figure 16:
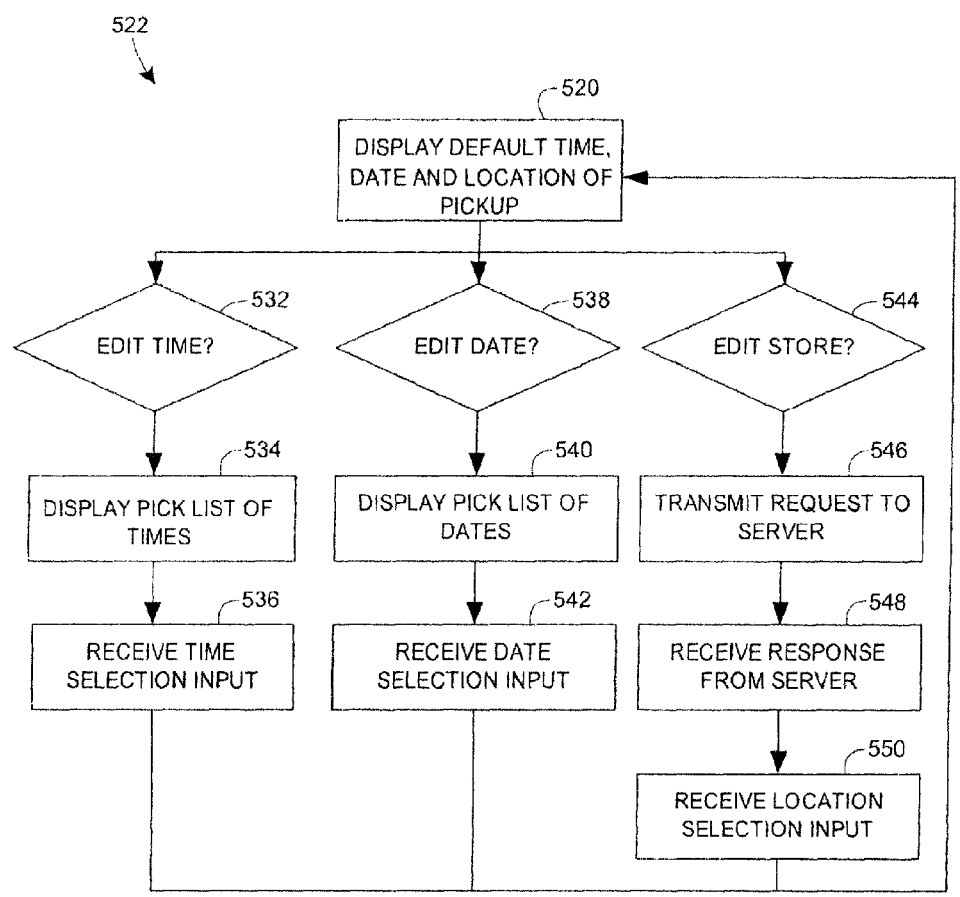
FIG. 16 depicts an exemplary method corresponding to a portion of the method depicted in FIG. 15.

FIG. 16 depicts a method corresponding to the blocks 520-522 of FIG. 15. As described the mobile device application displays the default time, date, and location of pickup (block 520). If the user selects to edit the time (block 532), the mobile device application displays a pick list of times (block 534) and then receives the time selection input from the user (block 536) before returning the display to the time, date, and location of pickup (block 520) (though no longer the default time). Similarly, if the user selects to edit the date (block 538), the mobile device application displays a pick list of dates (block 540) and then receives the date selection input from the user (block 542) before returning the display to the time, date, and location of pickup (block 520). Lastly, if the user selects to edit the pickup store (block 544), the mobile device application may transmit a request to a store finder service/routine (block 546) which may run on a server. The mobile device application may receive a response from the service/routine (block 548). After receiving a pickup location selection input from the user (block 550), the mobile device application may return the user to the time, date, and location screen (block 520).

It should be recognized that different mobile devices may implement different mechanisms for user input. In the examples described above, the mobile phone is assumed to have a touch sensitive display screen. Accordingly, "buttons" which are displayed on the screen and are not physical buttons, are "pressed" by touching the screen in the area of the button. However, those of ordinary skill in the art will readily appreciate that such user interface controls may be accomplished in other manners, such as using soft-keys, navigating controls using navigation buttons on a keyboard or using a roller ball, selecting numbers corresponding to different controls, entering information on a keyboard, etc.

This detailed description is to be construed as exemplary only and does not describe every possible embodiment, as describing every possible embodiment would be impractical, if not impossible. One could implement numerous alternate embodiments, using either current technology or technology developed after the filing date of this application.

We claim:

1. A method for allowing a customer to refill a prescription with an application executing on a web enabled mobile device, where the web enabled mobile device includes a processor, a memory coupled to the processor and a camera configured to capture a barcode image that has at least a prescription number encoded therein, the method comprising:

causing the processor to display an interface in the application executing on the web enabled mobile device, the interface for selection of a prescription refill option;

receiving an input at the processor from the customer indicating, via the application, a selection of the prescription refill option;

the application causing the processor to activate the web enabled mobile device's camera for scanning of a barcode;

the application causing automatically or upon a user input, the camera to capture an image, displayed in the application, of the barcode indicating at least a prescription number, the prescription number corresponding to a prescription medication and a patient;

the application causing the processor to transmit from the application, over a network, to a server, data indicative of at least the prescription number so that the server can automatically validate the prescription number by verifying that the prescription number exists in a database of prescription numbers corresponding to a previously filled prescription medication;

receiving information at the web enabled mobile device, over the network, at least a portion of which is to be displayed in an order review page of the application executing on the web enabled mobile device;

causing the processor to generate a display in the application including the at least the portion of received information in an order review page, wherein the information includes the prescription number and a pharmacy location where the prescription medication in the prescription will be filled;

wherein the information to be displayed in the order review page includes the pharmacy location and an option to change the pharmacy location;

transmitting from the web enabled mobile device, in response to an action by the customer viewing the displayed order review page, to the server and via the network, a confirmation to refill the prescription.

2. The method of claim 1, wherein receiving data corresponding to the prescription information to be displayed in an order review page further comprises receiving a default pickup time and a default pickup date.

3. The method of claim 2, wherein causing the processor to generate the display comprises displaying an option to facilitate a change by the customer to the default pickup time and the default pickup date before transmitting the order confirmation.

4. The method of claim 1, further comprising receiving at the web enabled mobile device the validation of the prescription number.

5. The method of claim 1, wherein causing the processor to generate the display comprises displaying either the most recent pharmacy location at which the prescription medication was filled or a default location for a patient associated with the prescription number.

6. The method of claim 1, further comprising causing the processor to generate another display that includes an identified area to assist the customer in positioning the web enabled mobile device's camera over the barcode.

7. The method of claim 6, wherein causing the camera to capture the image of the barcode comprises causing the processor to automatically recognize that the barcode is present in the identified area.

8. The method of claim 1, wherein causing the camera to capture the image of the barcode indicating at least a prescription number further comprises causing the processor to decode the barcode to determine the prescription number.

9. The method of claim 1, wherein causing the processor to transmit, over the network, to the server, data indicative of at least the prescription number comprises transmitting the captured image, over the network, to the server and further comprises receiving at the web enabled mobile device at least the prescription number that was decoded at the server from the captured image.

10. A nontransitory, computer-readable storage medium having computer-executable instructions stored in a memory, the instructions to be executed on a processor in a web enabled mobile device for providing an application operable to allow a user access to a refill by scan prescription system, the computer executable instructions comprising instructions for:
  causing the processor to generate a first display in the application executing on the web enabled mobile device to allow a user to order a prescription refill from within the application;
  the application causing the processor to activate a camera in the application executing on the web enabled mobile device to scan a barcode automatically or in response to a user input;
  the application causing the camera to capture an image of the barcode indicating at least a prescription number;
  the application causing the processor to transmit from the application executing on the web enabled mobile device at least data indicative of the prescription number to a pharmacy server so that the server can verify the prescription number by verifying that the prescription number exists in a database of prescription numbers corresponding to previously filled prescription medications;
  receiving over a network at the web enabled mobile device prescription pickup information when the prescription number was verified;
  the application causing the processor to generate a second display in the application, the second display including the prescription pickup information on the web enabled mobile device;
  wherein the prescription pickup information to be displayed in the second display of the application includes a pharmacy pickup location and an option to change the pharmacy pickup location;
  receiving at the web enabled mobile device, via the application, a confirmation input from the user;
  the application causing the processor to transmit from the web enabled mobile device confirmation information to the server;
  receiving at the web enabled mobile device order receipt information from a server; and
  causing the processor to generate a third display in the application, the third display including the order receipt information on the web enabled mobile device.

11. The computer-readable storage medium of claim 10, comprising further instructions for:
  causing the processor to transmit stored contact information to the pharmacy server, the stored contact information comprising one of: a stored email address, a phone number associated with the web enabled mobile device, and a device identification other than a phone number.

12. The computer-readable storage medium of claim 10, comprising further instructions for:
  causing the processor to generate on one of the displays an option to facilitate a change by the user to a default pickup time and a default pickup date before transmitting the confirmation information.

13. The method of claim 10, wherein causing the camera to capture the image of the barcode comprises causing the processor to automatically recognize that the barcode is present.

14. A system for receiving a refill order for one or more prescription medications, the system comprising:
  a communication network;
  one or more web enabled mobile devices, each web enabled mobile device having a processor, a memory coupled to the processor and a camera coupled to the processor and the memory; and
  one or more server computers communicatively coupled to the communication network and the one or more web enabled mobile devices;
  one of the one or more web enabled mobile devices having an application stored thereon;
  the application configured to cause the processor to display an interface in the application executing on the web enabled mobile device, the interface for selection of a prescription refill option;
  the application configured to receive an input at the processor from the customer indicating, via the application, a selection of the prescription refill option;
  the application configured to cause the processor to activate the web enabled mobile device's camera for scanning of a barcode;
  the application configured to cause, automatically or upon a user input, the camera to capture an image, displayed in the application, of the barcode indicating at least a prescription number, the prescription number corresponding to a prescription medication and a patient;
  the application configured to cause the processor to transmit from the application, over the communication network, to at least one of the one or more server computers, data indicative of at least the prescription number so that the server can automatically validate the prescription number by verifying that the prescription number exists in a database of prescription numbers corresponding to a previously filled prescription medication;

the application configured to receive information at the web enabled mobile device, over the communication network, at least a portion of which is to be displayed in an order review page of the application executing on the w enabled mobile device;

the application configured to cause the processor to generate a display in the application including the at least the portion of received information in an order review page, wherein the information includes the prescription number and a pharmacy location where the prescription medication in the prescription will be filled;

the application configured to transmit from the web enabled mobile device, in response to an action by the customer viewing the displayed order review page, to at least one of the one or more server computers and via the communication network, a confirmation to refill the prescription.

15. The system of claim 14, wherein at least one of the one or more server computers is further configured to transmit to the customer's web enabled mobile device data corresponding to a default pickup time and a default pickup date, wherein the default pickup time and the default pickup date are editable by the customer before confirming the order.

16. The system of claim 15, wherein the application is further configured to allow the customer to edit the default pickup time and the default pickup date before confirming the order.

17. The system of claim 14, wherein at least one of the one or more server computers is further configured to retrieve a default pharmacy location for a patient associated with the prescription number.

18. The system of claim 14, wherein at least one of the one or more server computers is further configured to receive a store number from the web enabled mobile device and associate the store number with a particular pharmacy location.

19. The system of claim 14, wherein at least one of the one or more server computers is further configured to electronically transmit the prescription refill order to the determined pharmacy location.

* * * * *